US005824304A

United States Patent [19]
Papayannopoulou

[11] Patent Number: 5,824,304

[45] Date of Patent: Oct. 20, 1998

[54] PERIPHERALIZATION OF HEMATOPOIETIC STEM CELLS

[76] Inventor: Thalia Papayannopoulou, 702 35th Ave., Seattle, Wash. 98122

[21] Appl. No.: 463,298

[22] Filed: Jun. 5, 1995

Related U.S. Application Data

[60] Division of Ser. No. 436,339, Nov. 15, 1993, which is a continuation-in-part of Ser. No. 977,702, Nov. 13, 1992, abandoned.

[51] Int. Cl.[6] ......................... A61K 39/395; A61K 38/19

[52] U.S. Cl. ..................................... 424/132.1; 424/140.1; 424/144.1; 424/156.1; 424/85.1; 530/388.85; 530/389.6

[58] Field of Search ............................... 424/85.1, 130.1, 424/144.1, 156.1, 140.1; 530/388.85, 389

[56] References Cited

U.S. PATENT DOCUMENTS 5,061,620 10/1991 Tsukamato et al. .

FOREIGN PATENT DOCUMENTS 0 455 482 11/1991 European Pat. Off. .

OTHER PUBLICATIONS

Andrews et al., "A C—Kit Ligand, Recombinant Human Stem Cell Factor, Mediates Reversible Expansion of Multiple CD34+ Colony—Forming Cell Types In Blood and Marrow of Baboons", *Blood* 80, pp. 920–927 (1992).

Bronchud et al., "In Vitro and In Vivo Analysis of the Effects of Recombinant Human Granulocyte Colony–Stimulating Factor in Patients", *Br.J.Cancer, 58,* pp. 65–69 (1988).

Bensinger et al., "Autologous Transplantation With Peripheral Blood Mononuclear cells Collected After Administration of Recombinant Granulocyte Stimulating Factor", *Blood,* 81, No. 11, pp. 31–58–3163 (1993).

Berenson, "Transplantation of CD34+ Hematopoietic Precursors: Clinical Rationale", *Transplantation Proceedings,* 24, No. 6, pp. 3032–3034 (1992).

Bregni et al., "Human Peripheral Blood Hematopoietic Progenitors Are Optimal Targets of Retroviral—Mediated Gene Transfer", *Blood,* 80, N. 6, pp. 1418–1422 (1992).

Brugger et al., "Ex Vivo Expansion of Enriched Peripheral Blood CD34+ Progenitor Cells by Stem Cell Factor, Interleukin–1β (IL—1β), IL—6, IL—3, Interferon—∂, and Erythropoietin", *Blood,* 81, no. 10, pp. 2579–2584 (1993).

Chao et al., "Granulocyte Colony–Stimulating Factor 'Mobilized' Peripheral Blood Progenitor Cells Accelerate Granulocyte and Platelet Recovery After High–Dose Chemotherapy", *Blood,* 81, No. 8, pp. 2031–2035 (1993).

Craig et al., "peripheral Blood Stem Cell Transplantation", *Blood Review,* 6:, pp. 59–67 (1992).

DePalma, "CellPro, Inc. Tests Its Stem Cell–Therapy in Clinic Trials", *Genetic Engineering News,* vol. 12 (May 1, 1992).

Denkers et al., "VLA Molecule Express May Be Involved in the Release of Acute Myeloid Leukaemic Cells From the Bone Marrow", *Leukemia Research,* 16, pp. 469–474 (1992).

Edington, "New Horizons for Stem—Cell Bioreactors", *Biotechnology,* 10, pp. 1099–1106 (1992).

Gale et al., "Blood Stem Cell Transplants Come of Age", *Bone Marrow Transplantation,* 9, pp. 151—155 (1992).

Gerhartz, "Zukunftsperspektiven von Knochenmarkund Stammzellaktivierung fur die autologe Transplantation", *Beitr Infusionther,* 28, pp. 254–309 (1991).

Haas, "Successful Autologous transplantaion of Blood Stem Cells Mobilized with Recombinant Human Granulocyte—Macrophage Colony—Stimulating Factor", *Exp. Hematol.,* 18, pp. 94–98 (1990).

Kessinger et al., "The Evolving Role of Autologous Peripheral Stem Cell Transplantation Following High–Dose Therapy for Malignancies", *Blood,* 77, No. 2, pp. 211–213 (1991).

Korbling, "Die Rolle der Stammzell—Mobilisation im Rahmen der Autologen Blutstammzell—Transplantation", *Beitr. Infusionther.,* 28, 233–241 (1991).

Liesveld et al., "Expression of Integrins and Examination of Their Adhesive Function in Normal and Leukemic Hematopoietic Cells", *Blood,* 81, pp. 112–121 (1993).

Lobo et al., "Addition of Peripheral Blood Stem Cells Collected Without Mobilization Techniques to Transplanted Autologous Bone Marrow Did Not Hasten Marrow Recovery Following Myeloablative Therapy", *Bone Marrow Transplantation,* 8, pp. 389–392 (1992).

Magrin et al., "Collection, Processing and Storage of Peripheral Blood Stem Cells (PBSC)", *Hematologica,* 76, Suppl. 1, pp. 55–57 (1991).

Papayannopoulou et al., "Peripheralization of hemopoietic Progenitors in Primates Treated with Anti—VLA4 Integrin", *Proc. Natl. Acad. Sci. USA,* 90, pp. 9374–9378 (1993).

Rowe et al., "Hemopoietic Growth Factors; A Review", *J. Clin.Pharmacol,* 32, pp. 486–501 (1992).

Ryan et al., "Inhibition of Human Bone Marrow Lymphoid Progenitor Colonies by Antibodies to VLA Integrins", *J.Immunol.,* 149, 11, pp. 3759–3764 (1992).

Siena et al., "Circulation of CD34+ Hematopoietic Stem Cells in the Peripheral Blood of High–Dose Cyclophosphamide—Treated Patients: Enhanced by Intravenous Recombinant Human Granulocyte—Macrophage Colony–Stimulating Factor", *Blood,* 74, No. 6, pp. 1905–1914 (1989).

(List continued on next page.)

*Primary Examiner*—Lila Feisee
*Assistant Examiner*—Nancy A. Johnson
*Attorney, Agent, or Firm*—Kerry A. Flynn

[57] ABSTRACT

The invention provides methods for peripheralizing $CD34^+$ cells, including hematopoietic stem cells. In a first aspect, the method comprises the step of administering a blocking agent of VLA-4 antigen on the surface of $CD34^+$ cells. In a second aspect, the method comprises administering a blocking agent of VLA-4 antigen on the surface of $CD34^+$ cells and administering a stimulating agent of $CD34^+$ cell proliferation in vivo. The method according to the invention is useful in the treatment of cancer or AIDS, and in gene therapy.

12 Claims, 12 Drawing Sheets

OTHER PUBLICATIONS

Simmons et al., "Vascular Cell Adhesion Molecule—1 Expressed by Bone Marrow Stromal Cells Mediates the Binding of Hematopieotic Progenitor Cells", *Blood,* 80, 388—395 (1992).

Stewart et al., "Post—5—Fluorouracil Human Marrow: Stem Cell characteistics and Renewwal Properties After Autologous Marrow Transplantation", *Blood,* 81, No. 9, pp. 2283–2289 (1993).

Teixido et al., "Human CD34+ Progenitor Cell Adhesion to Marrow Stroma is Mediated by VLA—4/VCAM and VLA5/Fibronectin", *Blood,* 78, Suppl. 1, p. 302a, abstract 1200 (1991).

Teixido et al., "Role of β1 and β2 Integrins in the Adhesion of Human CD34hi Stem Cells to Bone Marrow Stroma", *J. Clin. Invest.,* 90, pp. 358–367 (1992).

Williams et al., "Fibronectin and VLA—4 in hematopoietic Stem Cells—Microenvironment Interactions", *Nature,* 352, pp. 438–441 (1991).

Fox, Biotechnology V12 p. 128 Feb. 12, 1994.

Terstoppen Blood 77:1218–1227, 1991.

Kerr, J. of School Health 60:76–77 1990.

Levinsky Clin. Imm & Immunopath 50:5124–132 1989.

Lane, Annals of Internal Medicine 103:714–718, 1985.

Pulido J. Biol. Chem. 266:1024–10249, 1991.

GTCAAACTGCAGCAGTCTGGGGCAGAGCTTGTGAAGCCAGGGGCCTCAGT

CAAGTTGTCCTGCACAGCTTCTGGCTTCAACATTAAAGACACCTATATGC

ACTGGGTGAAGCAGAGGCCTGAACAGGGCCTGGAGTGGATTGGAAGGATT

GATCCTGCGAGTGGCGATACTAAATATGACCCGAAGTTCCAGGTCAAGGC

CACTATTACAGCGGACACGTCCTCCAACACAGCCTGGCTGCAGCTCAGCA

GCCTGACATCTGAGGACACTGCCGTCTACTACTGTGCAGACGGAATGTGG

GTATCAACGGGATATGCTCTGGACTTCTGGGGCCAAGGGACCACGGTCAC

CGTCTCCTCA

FIG. 5A

AGTATTGTGATGACCCAGACTCCCAAATTCCTGCTTGTTTCAGCAGGAGA
CAGGGTTACCATAACCTGCAAGGCCAGTCAGAGTGTGACTAATGATGTAG
CTTGGTACCAACAGAAGCCAGGGCAGTCTCCTAAACTGCTGATATATTAT
GCATCCAATCGCTACACTGGAGTCCCTGATCGCTTCACTGGCAGTGGATA
TGGGACGGATTTCACTTTCACCATCAGCACTGTGCAGGCTGAAGACCTGG
CAGTTTATTTCTGTCAGCAGGATTATAGCTCTCCGTACACGTTCGGAGGG
GGGACCAAGCTGGAGATC

FIG. 5B

ATG GAC TGG ACC TGG AGG GTC TTC TGC TTG CTG GCT GTA GCA CCA GGT
GCC CAC TCC CAG GTC CAA CTG CAG GAG AGC GGT CCA GGT CTT GTG AGA
CCT AGC CAG ACC CTG AGC CTG ACC TGC ACC GTG TCT GGC TTC AAC ATT
AAA GAC ACC TAT ATG CAC TGG GTG AGA CAG CCA CCT GGA CGA GGT CTT
GAG TGG ATT GGA AGG ATT GAT CCT GCG AGT GGC GAT ACT AAA TAT GAC
CCG AAG TTC CAG GTC AGA GTG ACA ATG CTG GTA GAC ACC AGC AAG AAC
CAG TTC AGC CTG AGA CTC AGC AGC GTG ACA GCC GCC GAC ACC GCG GTC
TAT TAT TGT GCA GAC GGA ATG TGG GTA TCA ACG GGA TAT GCT CTG GAC
TTC TGG GGC CAA GGG ACC ACG GTC ACC GTC TCC TCA GGT GAG TCC

FIG. 7A

Figure 7B:
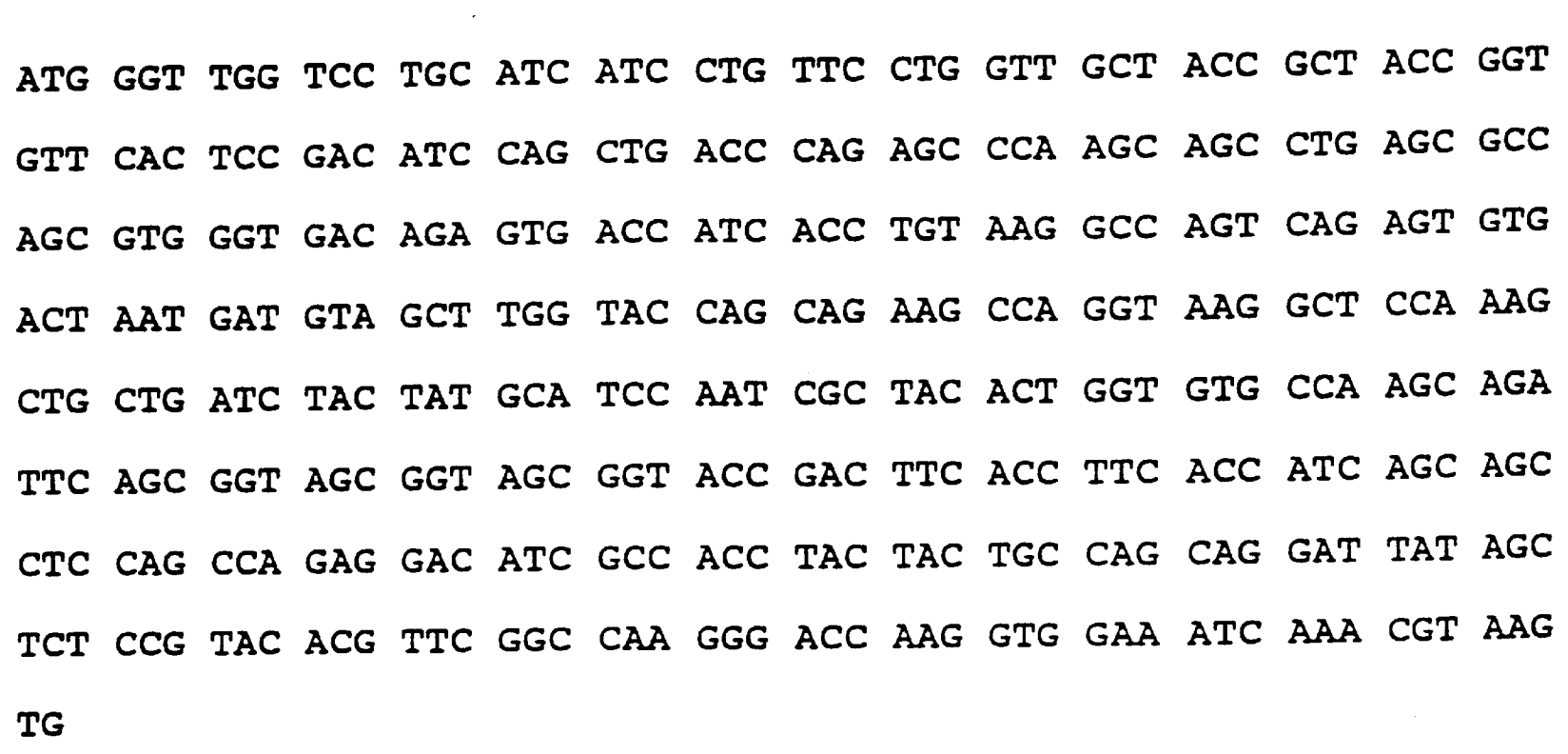

ATG GGT TGG TCC TGC ATC ATC CTG TTC CTG GTT GCT ACC GCT ACC GGT

GTT CAC TCC GAC ATC CAG CTG ACC CAG AGC CCA AGC AGC CTG AGC GCC

AGC GTG GGT GAC AGA GTG ACC ATC ACC TGT AAG GCC AGT CAG AGT GTG

ACT AAT GAT GTA GCT TGG TAC CAG CAG AAG CCA GGT AAG GCT CCA AAG

CTG CTG ATC TAC TAT GCA TCC AAT CGC TAC ACT GGT GTG CCA AGC AGA

TTC AGC GGT AGC GGT AGC GGT ACC GAC TTC ACC TTC ACC ATC AGC AGC

CTC CAG CCA GAG GAC ATC GCC ACC TAC TAC TGC CAG CAG GAT TAT AGC

TCT CCG TAC ACG TTC GGC CAA GGG ACC AAG GTG GAA ATC AAA CGT AAG

ATG GAC TGG ACC TGG AGG GTC TTC TGC TTG CTG GCT GTA GCA CCA GGT
GCC CAC TCC CAG GTC CAA CTG CAG GAG AGC GGT CCA GGT CTT GTG AGA
CCT AGC CAG ACC CTG AGC CTG ACC TGC ACC GCG TCT GGC TTC AAC ATT
AAA GAC ACC TAT ATG CAC TGG GTG AGA CAG CCA CCT GGA CGA GGT CTT
GAG TGG ATT GGA AGG ATT GAT CCT GCG AGT GGC GAT ACT AAA TAT GAC
CCG AAG TTC CAG GTC AGA GTG ACA ATG CTG GTA GAC ACC AGC AGC AAC
CAG TTC AGC CTG AGA CTC AGC AGC GTG ACA GCC GCC GAC ACC GCG GTC
TAT TAT TGT GCA GAC GGA ATG TGG GTA TCA ACG GGA TAT GCT CTG GAC
TTC TGG GGC CAA GGG ACC ACG GTC ACC GTC TCC TCA GGT GAG TCC

FIG. 8A

ATG GGT TGG TCC TGC ATC ATC CTG TTC CTG GTT GCT ACC GCT ACC GGT

GTC CAC TCC AGC ATC GTG ATG ACC CAG AGC CCA AGC AGC CTG AGC GCC

AGC GTG GGT GAC AGA GTG ACC ATC ACC TGT AAG GCC AGT CAG AGT GTG

ACT AAT GAT GTA GCT TGG TAC CAG CAG AAG CCA GGT AAG GCT CCA AAG

CTG CTG ATC TAC TAT GCA TCC AAT CGC TAC ACT GGT GTG CCA GAT AGA

TTC AGC GGT AGC GGT TAT GGT ACC GAC TTC ACC TTC ACC ATC AGC AGC

CTC CAG CCA GAG GAC ATC GCC ACC TAC TAC TGC CAG CAG GAT TAT AGC

TCT CCG TAC ACG TTC GGC CAA GGG ACC AAG GTG GAA ATC AAA CGT AAG

PERIPHERALIZATION OF HEMATOPOIETIC STEM CELLS

This is a division of copending application Ser. No. 08/436,339, filed Nov. 15, 1993 which is a continuation-in-part of abandoned application Ser. No. 07/977,702, filed Nov. 13, 1992.

FIELD OF THE INVENTION

The invention relates to the manipulation of hematopoietic stem cells. More particularly, the invention relates to methods for increasing the number of hematopoietic stem cells in peripheral blood.

BACKGROUND OF THE INVENTION

Hematopoietic stem cells are primitive, uncommitted progenitor cells that give rise to the lymphoid, myeloid and erythroid lineages of cells in blood. The stem cell population constitutes only a small proportion of the total cells in bone marrow and represents even a far more minuscule proportion of the cells in peripheral blood.

Stem cells have commonly been characterized by their surface antigenic determinants. Tsukamoto et al., U.S. Pat. No. 5,061,620 (1991), teaches that a highly stem cell concentrated cell composition is $CD34^+$, $CD10^-$, $CD19^-$ and $CD33^-$. Leon et al., Blood 77:1218–1227 (1991), teaches that about one per cent of $CD34^+$ cells, or about 0.01% of the total marrow cell population, do not express differentiation antigens, such as CD33 (myeloid lineage), CD71 (erythroid lineage) or CD10 and CD5 (lymphoid B and T lineage), and that reduced expression of CD34 expression during maturation is associated with increased expression of the differentiation antigens.

Combinations of antigenic and functional characteristics have also been used to characterize stem cells. Sutherland et al., Proc. Natl. Acad. Sci. U.S.A. 87:3584–3588 (1990), teaches that primitive stem cells do not bind to soybean agglutinin, express high levels of CD34, form blast colonies with high plating efficiency and are enriched in long-term culture initiating cells (LTC-IC). Craig et al., Blood Reviews 6:59–67 (1992), teaches that the CFU-GM assay is the most widely used measure of the hematopoietic progenitor viability of a bone marrow or peripheral blood stem cell harvest, and correlates well with per cent $CD34^+$. Spangrude, Immunology Today 10:344–350 (1989), teaches that stem cells accumulate low levels of rhodamine 123 relative to other bone marrow cell types. Chaudhaury et al., Cell 66:85–94 (1991), teaches that stem cells express high levels of P-glycoprotein relative to other marrow cell types.

The ability to manipulate hematopoietic stem cells has become increasingly important in the development of effective chemotherapeutic and radiotherapeutic approaches to the treatment of cancer. Current approaches to chemotherapy and radiotherapy utilize bone marrow transplantation (BMT). BMT involves removing one to two liters of viable pelvic bone marrow containing stem cells, progenitor cells and more mature blood cells, treating the patient with chemotherapy or radiotherapy to kill tumor cells, and reintroducing bone marrow cells intravenously. BMT, however, suffers from many disadvantages. Harvesting of BM for BMT requires general anaesthesia, which increases both risk and cost. In addition, if cancer cells are present in the marrow and are not rigorously purged, recurrence of the disease is a distinct risk. Also, if widespread invasion of bone marrow by cancer cells (myeloma, Waldenstrom's macroglobulinemia) is present, peripheral blood cells are the only option for use in autologous transplantation (ABMT). Finally, patients who have undergone pelvic irradiation are not candidates for ABMT.

As a result of these difficulties, much interest has been developed in providing methods for obtaining stem cells from peripheral blood for autologous supply of stem cells to patients undergoing chemotherapy. Autologous supply of stem cells from peripheral blood would allow the use of greater doses of chemo- or radiotherapy, but with less risk than BMT. In addition, the use of stem cells from peripheral blood does not require anaesthesia to obtain the stem cells. Also, Lowry, Exp. Hematol. 20:937–942 (1992), teaches that cancer cells in the marrow tend not to peripheralize. The critical limitation in such a procedure, however, lies in the very small number of stem cells ordinarily present in peripheral blood. Lobo et al., Bone Marrow Transplantation 8:389–392 (1991), teaches that addition of peripheral blood stem cells collected in the absence of any peripheralization techniques does not hasten marrow recovery following myeloablative therapy. In contrast, Haas et al., Exp. Hematol. 18:94–98 (1990), demonstrates successful autologous transplantation of peripheral blood stem cells mobilized with recombinant human granulocyte-macrophage colony-stimulating factor (GM-CSF). Thus, increasing the number of stem cells in peripheral blood by peripheralization techniques is critical to the success of procedures utilizing peripheral blood as a source for autologous stem cell transplantation. Other cytokines may be useful in this regard. Rowe and Rapoport, J. Clin. Pharmacol. 32:486–501 (1992), suggests that in addition to GM-CSF, other cytokines, including macrophage colony-stimulating factor (M-CSF), granulocyte colony-stimulating factor (G-CSF), erythropoietin, interleukins-1, -2, -3, -4 , and -6 , and various interferons and tumor necrosis factors have enormous potential.

Another approach to autologous transplantation is to purify stem cells from peripheral blood using immunoaffinity techniques. These techniques hold promise not only for autologous stem cell transplantation in conjunction with chemotherapy, but also for gene therapy, in which purified stem cells are necessary for genetic manipulation to correct defective gene function, then reintroduced into the patient to supply the missing function. However, Edgington, Biotechnology 10:1099–1106 (1992), teaches that current procedures require three separate four hour sessions to process enough cells in the absence of peripheralization. DePalma, Genetic Engineering News, Vol. 12, May 1, 1992, teaches that this can be improved by treatment with G-CSF for peripheralization.

These studies underscore the importance of developing new methods to effect the peripheralization of hematopoietic stem cells. One possibility is to search for new ways to release stem cells from the bone marrow environment into the periphery. Unfortunately, little is known about the types of molecular interactions that hold hematopoietic stem cells in the marrow environment in vivo. Recently, some in vitro studies have been undertaken to look at the role of integrins, fibronectin, and other surface antigens in binding between stem cells and bone marrow stromal cells.

Integrins are a large family of integral membrane glycoproteins having over 16 heterodimeric members that mediate interactions between cells, interactions between cells and the extracellular matrix, and interactions involved in embryonic development and regulation of T-cell responses. Among integrins, the VLA-5 ($\alpha^5\beta_1$) complex is widely distributed and functions as a receptor for fibronectin. The VLA-4 ($\alpha^4\beta_1$) complex is expressed at substantial levels on normal peripheral blood B and T cells, thymocytes, monocytes, and some melanoma cells as well as on marrow blast cells and erythroblasts. Ligands for VLA-4 are vascular cell adhesion molecule-1(VCAM-1) and CS-1, an alternately spliced domain within the Hep II region of fibronectin. Another group of integrins (CDIIa/CD18, CDIIb/CD18, and CDIIc/CD18) share the common $\beta_2$ chain and are variably expressed on peripheral T cells, monocytes, and mature granulocytes. Ligands for $\beta_2$-integrins include members of the Ig superfamily (ICAM-1 and ICAM-2) found on activated endothelial cells.

Teixido et al., J. Clin. Invest. 90:358–367 (1992), teaches that in an in vitro model, interactions between VLA-4/VCAM-1, VLA-5/fibronectin and $\beta_2$-integrin/ICAM-1 are all important for adhesion between bone marrow stromal cells and cells expressing high levels of CD34. Simmons et al., Blood 80:388–395 (1992), teaches that in an in vitro model, adhesion between stromal cells and $CD34^+$ cells was predominantly dependent on the VLA-4/VCAM-1 interaction and was largely inhibited by monoclonal antibodies to either VLA-4 or VCAM-1, with fibronectin playing a minor role in binding. Williams et al., Nature 352:438–441 (1991), using in vivo mouse studies, teaches that adhesion of murine hematopoietic stem cells to stromal cell extracellular matrix (ECM) is partly promoted by proteolytic fragments of fibronectin containing an alternatively spliced region of the IIICS domain, and suggests that the interaction is likely to be mediated by VLA-4. All of these studies utilized antibodies to prevent adherence between stem cells and their microenvironment. However, none have analyzed whether such interactions are reversible, or perturbable after adherence has taken place. These results indicate the need for further studies to determine what interactions between the bone marrow environment and hematopoietic stem cells are responsible for keeping the stem cells within that environment in vivo and whether such interactions can be perturbed to effect peripheralization of stem cells.

There is, therefore, a need for new methods for peripheralizing stem cells, both for scientific investigatory purposes for understanding the processes of peripheralization and homing, and for the development of better methods of peripheralization for autologous stem cell transplantation in the course of cancer treatment or gene therapy. Preferably, such methods should produce even higher levels of stem cells in peripheral blood than existing methods provide.

BRIEF SUMMARY OF THE INVENTION

In a first aspect, the invention provides a novel method for increasing the number of hematopoietic stem cells and $CD34^+$ cells in peripheral blood, which is also known as "peripheralization" or "mobilization" of hematopoietic stem cells and $CD34^+$ cells. This method comprises the step of administering a blocking agent of VLA-4 antigens on the surface of hematopoietic stem cells and $CD34^+$ cells. Various agents can be used to mediate such blocking, including anti-VLA-4 or anti-VCAM-1 antibodies which may optionally be single chain, humanized or chimeric, Fab, Fab', $F(ab')_2$ or F(v) fragments thereof, heavy or light chain monomers or dimers thereof, or intermixtures of the same, soluble fibronectin, CS-1 peptides or fibronectin peptides containing the amino acid sequence EILDV or conservatively substituted amino acid sequences, or soluble VCAM-1, bifunctional VCAM-1/Ig fusion proteins or VCAM-1 peptides.

In another aspect, the invention provides a novel method for peripheralizing hematopoietic stem cells and $CD34^+$ cells with more predictable greater effectiveness than cytokine treatment alone provides. According to this aspect of the invention, the method comprises administering a blocking agent of VLA-4 antigens on the surface of hematopoietic stem cells and $CD34^+$ cells, as in the first aspect of the invention, in combination with a stimulating agent of hematopoietic stem cell proliferation. The step of administering a stimulating agent of hematopoietic stem cell proliferation can be carried out by using a cytokine, preferably G-CSF, stem cell factor, totipotent stem cell factor, stem cell proliferation factor or GM-CSF, but alternatively M-CSF, erythropoietin, interleukins-1, -2, -3, -4, -6, or 11.

In another aspect, the invention provides an improved method of transplanting peripheral blood stem cells into a patient who has undergone chemotherapy or radiotherapy for cancer. In this method, prior to the administration of myeloablative chemotherapy or radiotherapy, stem cells are peripheralized from the patient's bone marrow by administration of an agent that mediates blocking of VLA-4 antigens on the surface of hematopoietic stem cells and $CD34^+$ cells. This agent may be administered alone, or preferably in conjunction with an agent that stimulates proliferation of stem cells. The peripheralized stem cells are then collected from peripheral blood by leukapheresis. Stem cells are then enriched from the collected peripheralized blood by immunoadsorption using anti-CD34 antibodies. Optionally, the enriched stem cells are then expanded ex vivo by culturing them in the presence of agents that stimulate proliferation of stem cells. Following administration of myeloablative chemotherapy or radiotherapy, the enriched, and optionally expanded stem cells are then returned to the patient's circulating blood and allowed to engraft themselves into the bone marrow.

In another aspect, the invention provides an improved method of transplanting peripheral blood stem cells into a patient who has undergone myeloablative chemotherapy or radiotherapy for AIDS. This method involves the same steps as described for transplanting peripheralized stem cells into a patient who has undergone chemotherapy or radiotherapy for cancer. In addition, this method further optionally involves administration to the patient of anti-HIV agents, such as antivirals such as AZT, soluble CD4, and CD4-directed blockers of the AIDS virus or antisense or antigene oligonucleotides, both before and after the return of the enriched and optionally expanded stem cells to the patient's circulating blood. This step serves a "mopping up" function to prevent residual virus from infecting the progeny of the newly returned stem cells.

In another aspect, the invention provides an improved method for carrying out gene therapy in patients having various genetic and acquired diseases. In this method, stem cells are peripheralized from the patient's bone marrow by administration of an agent that mediates blocking of VLA-4 antigens on the surface of hematopoietic stem cells and $CD34^+$ cells. As in the method previously described herein, this agent may be administered alone or in conjunction with an agent that stimulates proliferation of stem cells. Peripheral blood is then collected by leukapheresis. Stem cells are then enriched from the collected peripheral blood by immunoadsorption using anti-CD34 antibodies. Optionally, the enriched stem cells are then expanded ex vivo by culturing them in the presence of agents that stimulate proliferation of stem cells. The enriched and optionally expanded stem cells are then transduced with an amphotrophic retroviral vector, or other suitable vectors, that expresses a gene that ameliorates the genetic or acquired disease. Optionally, the vector may also carry an expressed selectable marker, in which case successfully transduced cells may be selected for the presence of the selectable marker. The transduced and optionally selected stem cells are then returned to the patient's circulating blood and allowed to engraft themselves into the bone marrow.

It is an object of the invention to provide a method for peripheralizing hematopoietic stem cells and $CD34^+$ cells as an experimental model for investigating hematopoiesis, homing of stem cells to the bone marrow, and cytokine-induced peripheralization of stem cells. It is a further object of the invention to provide a method for optimizing peripheralization of hematopoietic stem cells and $CD34^+$ cells to provide stem cell-enriched peripheral blood for autologous transplantation following chemo- or radiotherapy. It is a further object of the invention to provide a method for peripheralizing $CD34^+$ cells to maximize the yield of purified hematopoietic stem cells and progenitor cells from peripheral blood, either for autologous transplantation of the stem cells following chemo- or radiotherapy, or for use in gene therapy. It is a further object of the invention to provide a method for peripheralizing stem cells and $CD34^+$ cells without risk of causing cytokine-induced cell differentiation of normal stem cells or proliferation of contaminating leukemia cells. It is a further object of the invention to provide a peripheralization technique that has predictable timing for the peak of progenitor content in peripheral blood for scheduling leukapheresis.

The invention satisfies each of these objects by providing a method for peripheralizing stem cells and $CD34^+$ cells by administering a blocking agent of VLA-4 antigen on the surface of hematopoietic stem cells. This effect can be increased by the use of such blocking agents in conjunction with approaches to amplify stem cells to produce a synergistic effect.

BRIEF DESCRIPTION OF THE DRAWINGS

In the following Figures, which further exemplify the claimed invention, dashed lines represent total white blood cell counts, as recorded on the right vertical axes. Black boxes represent BFUe, as represented on the left vertical axes. Downward arrows represent points of administration of antibody. Horizontal axes represent days before and after first administration of antibody.

FIG. 5 is the nucleotide sequences encoding the variable heavy region of the heavy and light chains of anti-VLA-4 murine monoclonal antibody HP1/2.

FIG. 7A is the nucleotide sequences of the $^{V}{}_{H}$-encoding regions having CDR-encoding sequences from murine HP1/2 transplanted therein.

FIG. 7B is the nucleotide sequence of the transplanted $^{V}{}_{K}$ sequence.

FIG. 8A is a nucleotide sequences encoding the variable regions of the heavy and light chains of the humanized anti-VLA-4 antibody hHP1/2 encoding the $^{V}{}_{H}$ region.

FIG. 8B is the nucleotide sequence encoding the $^{V}{}_{K}$ region.

DETAILED DESCRIPTION OF THE PREFERRED EMBODIMENTS

Figure 1A:
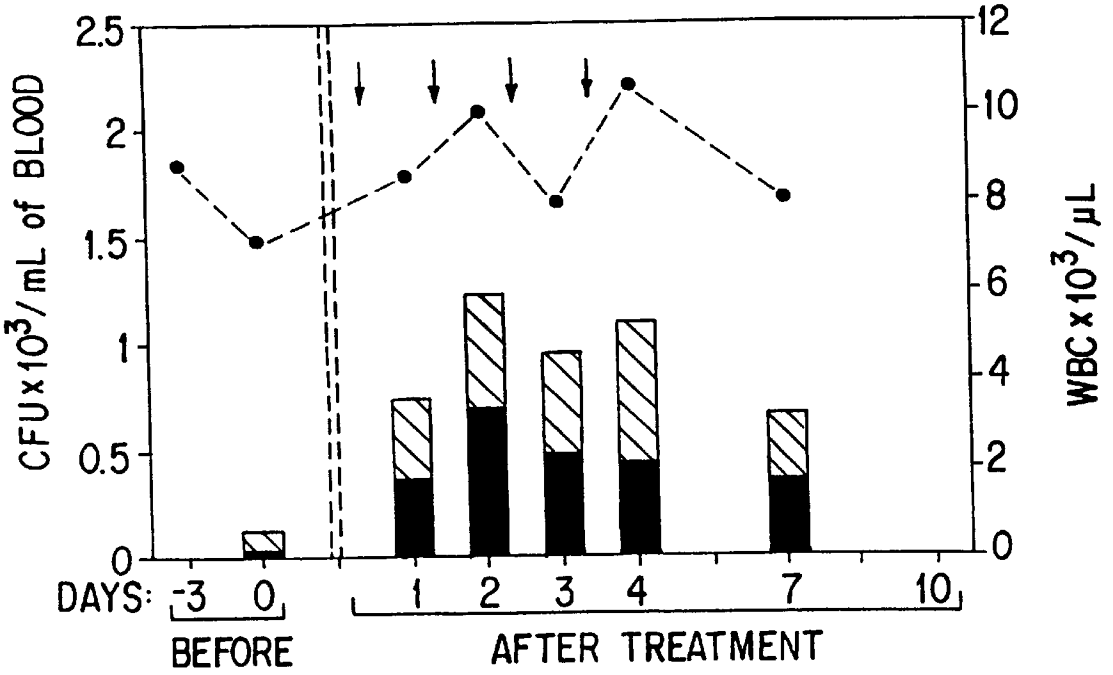
FIG. 1A is a profile of total white blood cells and CFU in peripheral blood before treatment of macaques.

The invention relates to the manipulation of hematopoietic stem cells. More particularly, the invention relates to the peripheralization of hematopoietic stem cells and other $CD34^+$ cells.

In a first aspect, this invention provides a method for peripheralizing hematopoietic stem cells and $CD34^+$ cells, comprising the step of administering a blocking agent of VLA-4 antigens on the surface of hematopoietic stem cells and $CD34^+$ cells. For purposes of this invention, the term "blocking agent of VLA-4 antigens" is intended to mean an agent that is capable of interfering with interactions between VLA-4 antigens and either VCAM-1 or fibronectin on the surface of stromal cells or in the extracellular matrix (ECM). As demonstrated herein, such blocking of VLA-4 antigens causes peripheralization of stem cells and $CD34^+$ cells. This demonstration utilized a monoclonal antibody against VLA-4 as a blocking agent. Those skilled in the art will recognize that, given this demonstration, any agent that can block VLA-4 antigens can be successfully used in the method of this invention. Thus, for purposes of this invention, any agent capable of blocking VLA-4 antigens on the surface of hematopoietic stem cells is considered to be an equivalent of the monoclonal antibody used in the examples herein. For example, this invention contemplates as equivalents at least peptides, peptide mimetics, carbohydrates and small molecules capable of blocking VLA-4 antigens on the surface of $CD34^+$ cells or hematopoietic stem cells.

In a preferred embodiment, the blocking agent that is used in the method of this invention to block VLA-4 antigens on the surface of hematopoietic stem cells and $CD34^+$ cells is a monoclonal antibody or antibody derivative. Preferred antibody derivatives include humanized antibodies, chimeric antibodies, single chain antibodies, Fab, Fab', $F(ab')_2$ and F(v) antibody fragments, and monomers or dimers of antibody heavy or light chains or intermixtures thereof. The successful use of monoclonal antibody OKT3 to control allograft rejection indicates that, although humanized antibodies are preferable, murine monoclonal antibodies can be effective in therapeutic applications. Monoclonal antibodies against VLA-4 are a preferred blocking agent in the method according to this invention. Human monoclonal antibodies against VLA-4 are another preferred blocking agent in the method according to the invention. These can be prepared using in vitro-primed human splenocytes, as described by Boerner et al., J. Immunol. 147:86–95 (1991). Alternatively, they can be prepared by repertoire cloning as described by Persson et al., Proc. Natl. Acad. Sci. U.S.A. 88:2432–2436 (1991) or by Huang and Stollar, J. of Immunol. Methods 141:227–236 (1991). Another preferred blocking agent in the method of the present invention is a chimeric antibody having anti-VLA-4 specificity and a human antibody constant region. These preferred blocking agents can be prepared according to art-recognized techniques, as exemplified in U.S. Pat. No. 4,816,397 and in Morrison et al., Proc. Natl. Acad. Sci. U.S.A. 81:6851–6855 (1984). Yet another preferred blocking agent in the method of this invention is a humanized antibody having anti-VLA-4 specificity. Humanized antibodies can be prepared according to art-recognized techniques, as exemplified in Jones et al., Nature 321:522 (1986); Riechmann, Nature 332:323 (1988); Queen et al., Proc. Natl. Acad. Sci. U.S.A. 86:10029 (1989); and Orlandi et al., Proc. Natl. Acad. Sci. U.S.A. 86:3833 (1989). Those skilled in the art will be able to produce all of these preferred blocking agents, based upon the nucleotide sequence encoding the heavy and light chain variable regions of HP1/2 [SEQ. ID. NOS. 1 and 2], as shown in FIG. 5, using only well known methods of cloning, mutagenesis and expression (for expression of antibodies, see, e.g., Boss et al., U.S. Pat. No. 4,923,805). Two other preferred blocking agents are single chain antibodies, which can be prepared as described in U.S. Pat. No. 4,946,778, the teachings of which are hereby incorporated by reference; and biosynthetic antibody binding sites, which can be prepared as described in U.S. Pat. No. 5,091,513, the teachings of which are hereby incorporated by reference. Those skilled in the art will recognize that any of the above-identified antibody or antibody derivative blocking agents can also act in the method of the present invention by binding the receptor for VLA-4, thus acting as agents for blocking the VLA-4 antigen on the surface of hehematopoietic stem cells, within the meaning of this term for purposes of this invention. Thus, antibody and antibody derivative blocking agents according to this invention, as described above, include embodiments having binding specificity for VCAM-1 or fibronectin, since these molecules appear to either be important in the adhesion between stem cells and stromal cells or the extracellular matrix or interfere with traffic of stem cells through other tissues and blood.

In another preferred embodiment, the blocking agents used in the method according to this invention are not antibodies or antibody derivatives, but rather are soluble forms of the natural binding proteins for VLA-4. These blocking agents include soluble VCAM-1, bifunctional VCAM-1/Ig fusion proteins, or VCAM-1 peptides as well as fibronectin, fibronectin having an alternatively spliced non-type III connecting segment and fibronectin peptides containing the amino acid sequence EILDV or a similar conservatively substituted amino acid sequence. These blocking agents will act by competing with the stromal cell- or ECM-bound binding protein for VLA-4 on the surface of stem cells.

In this method according to the first aspect of the present invention, blocking agents are preferably administered parenterally. The blocking agents are preferably administered as a sterile pharmaceutical composition containing a pharmaceutically acceptable carrier, which may be any of the numerous well known carriers, such as water, saline, phosphate buffered saline, dextrose, glycerol, ethanol, and the like, or combinations thereof. Preferably, the blocking agent, if an antibody or antibody derivative, will be administered at a dose between about 0.1 mg/kg body weight/day and about 10 mg/kg body weight/day. For non-antibody or antibody derivative blocking agents, the dose range should preferably be between molar equivalent amounts to these amounts of antibody. Optimization of dosages can be determined by administration of the blocking agents, followed by CFU-GM assay of peripheral blood, or assay of $CD34^+$ cells in peripheral blood. The preferred dosage should produce an increase of at least 10-fold in the CFU-GM counts in peripheral blood.

In a second aspect, the present invention provides a method for peripheralizing hematopoietic stem cells that is far more effective than cytokine treatment alone. According to this aspect of the invention, the method comprises the step of administering a blocking agent of VLA-4 antigens on the surface of hematopoietic stem cells in combination with the step of administering a stimulating agent of hematopoietic stem cell proliferation in vivo. The step of administering a blocking agent of VLA-4 antigens on the surface of hematopoietic stem cells is carried out in exactly the same fashion that is described for the first apsect of the invention. The step of administering a stimulating agent of hematopoietic stem cell proliferation in vivo is preferably carried out through the administration of cytokines.

Preferred cytokines for stimulating hematopoietic stem cells to proliferate include granulocyte colony-stimulating factor (G-CSF), stem cell factor, totipotent stem cell factor (TSCF), stem cell proliferation factor (SCPF), granulocyte-macrophage colony-stimulating factor (GM-CSF), macrophage colony-stimulating factor (M-CSF), erythropoietin, interleukin-1, -2, -3, -4, -6, and -11. Most preferred are G-CSF, stem cell factor and GM-CSF, because all three of these are known to cause proliferation of stem cells. The ability of G-CSF and GM-CSF to stimulate proliferation of progenitors is well established (see, e.g., Metcalf, Nature 339:27–30 (1989)), as is their ability to cause peripheralization of hematopoietic stem cells (see, e.g., Haas et al., Exp. Hematol. 18:94–98 (1990) and Blood 72:2074 (1988). This ability has also been established for stem cell factor (Andrews et al., Blood 80:920–927 (1992)). In addition, the enormous potential of these other cytokines identified herein has been recognized (see Rowe and Rapoport, J. Clin. Pharmacol. 32:486–501 (1992)). For purposes of this invention, stimulation of hematopoietic stem cells to proliferate can be carried out by any cytokine that is capable of mediating such proliferation in vivo. Thus, for purposes of this invention, any cytokine that can stimulate hematopoietic stem cells to proliferate in vivo is considered to be equivalent to G-CSF, stem cell factor and GM-CSF, which are also considered to be equivalent to each other. In addition, the use of chemotherapeutic agents alone can lead to the peripheralization of progenitors. Such agents can also be combined with VLA-4 blocking agents in the method according to the present invention.

In this method according to the second aspect of the invention, cytokines are preferably administered parenterally. The cytokines are preferably administered as a sterile pharmaceutical composition containing a pharmaceutically acceptable carrier, which may be any of the numerous well known carriers, such as water, saline, phosphate buffered saline, dextrose, glycerol, ethanol, and the like, or combinations thereof. Preferably, the cytokine, if G-CSF, will be administered at a dose between about 1 $\mu$g/kg body weight/day and about 50 $\mu$g/kg body weight/day, most preferably at about 10–15 $\mu$g/kg body weight/day. Most preferably, cytokines will be administered over a course of from about four to about ten days. Optimization of dosages or the combination of cytokines (e.g., G-CSF and kit ligand) can be determined by administration of the cytokine and administration of the blocking agents, followed by CFU-GM assay of peripheral blood. The preferred dosage should produce an increase of at least 5-fold in the CFU-GM counts per milliliter of peripheral blood, compared with cytokines alone.

According to this aspect of the present invention, the step of administering a blocking agent of VLA-4 antigens on the surface of hematopoietic stem cells or $CD34^+$ cells and the step of administering stimulating agents for proliferation of these cells can be carried out concomitantly or sequentially. In a preferred embodiment, the steps are carried out sequentially, preferably administering stimulating agents of $CD34^+$ or hematopoietic stem cell proliferation being the first step.

In a third aspect, this invention provides an improved method of transplanting peripheral blood stem cells into a patient who has undergone chemotherapy or radiotherapy for cancer. In this method, prior to the administration of chemotherapy or radiotherapy, stem cells are peripheralized from the patient's bone marrow by administration of an agent that mediates blocking of VLA-4 antigens on the surface of hematopoietic stem cells and $CD34^+$ cells. The blocking agents used in this method are preferably selected from those blocking agents described in the discussion of the first aspect of the invention. This agent may be administered alone, or in conjunction with an agent that stimulates proliferation of stem cells. The proliferation stimulating agents optionally used in this method are preferably selected from those proliferation stimulating agents described in the discussion of the second aspect of the invention. The peripheralized stem cells are then collected from peripheral blood by leukapheresis. Stem cells are then enriched from the collected peripheralized blood by CD34 affinity chromatography such as immunoadsorption using anti-CD34 antibodies. Such stem cell enrichment is known in the art and has been described, for example, by Berenson, Transplantation Proceedings 24:3032–3034 (1992) and the references cited therein. Optionally, the enriched stem cells are then expanded ex vivo by culturing them in the presence of agents that stimulate proliferation of stem cells. This ex vivo expansion can be carried out using, alone or in combination, any of the proliferation stimulating agents described in the discussion of the second aspect of the invention. Such ex vivo expansion of $CD34^+$ cells from peripheral blood is known in the art and has been described, for example, by Bruggar et al., Blood 81:2579–2584 (1993). Following administration of chemotherapy or radiotherapy, the enriched and optionally expanded stem cells are then returned to the patient's circulating blood and allowed to engraft themselves into the bone marrow.

The value of using peripheralized stem cells for transplantation after chemotherapy or radiotherapy for cancer is recognized in the art and has been described in numerous references, including Bensinger et al., Blood 81:3158–3163 (1993); Chao et al., 81:2031–2035 (1993); Kessinger and Armitage, Blood 77:211–213 (1991); Gale et al., Bone Marrow Transplantation 9:151–155 (1992); and Siena et al., Blood 74:1904–1914 (1989). The present method according to the invention provides an improvement in the transplantation of stem cells from peripheral blood by increasing the concentration of such stem cells in the peripheral blood, thereby greatly improving the likelihood of success of the transplantation.

In a fourth aspect, the present invention provides an improved method of transplanting purified peripheral blood stem cells into a patient who has undergone myeloablative chemotherapy or radiotherapy for AIDS. This method involves the same steps as described for transplanting peripheralized stem cells into a patient who has undergone chemotherapy or radiotherapy for cancer. In addition, this method further optionally involves administration to the patient of anti-HIV agents, such as antivirals such as AZT, soluble CD4, and CD4-directed blockers of the AIDS virus or antisense or antigene oligonucleotides, both before and after the return of the enriched and optionally expanded stem cells to the patient's circulating blood. This step serves a "mopping up" function to prevent residual virus from infecting the progeny of the newly returned stem cells.

The myeloablative chemotherapy or radiotherapy will generally be expected to destroy any cells in the blood that are infected by HIV. The "mopping up" step thus serves to remove any residual virus that otherwise could possibly infect the progeny of the stem cells transplanted into the patient after such therapy. Several agents can be useful in such a "mopping up" step. For example, CD4-directed anti-HIV agents and analogs have been shown to prophylactically prevent infection of uninfected $CD34^+$ cells by HIV. Similarly, anti-HIV oligonucleotides have been shown to prevent HIV infection of uninfected cells, for example in U.S. Pat. No. 4,806,463, the teaching of which are hereby incorporated by reference. Such oligonucleotides have been shown to prevent virus escape for up to a 100 day test period. See Lisziewicz et al., Proc. Natl. Acad. Sci. U.S.A. 90:3860–3864 (1993). Accordingly, this method according to the invention should provide a new therapeutic approach to AIDS.

In a fifth aspect, this invention provides an improved method for carrying out gene therapy in patients having any of a variety of genetic and acquired diseases. In this method, stem cells are peripheralized from the patient's bone marrow by administration of an agent that mediates blocking of VLA-4 antigens on the surface of hematopoietic stem cells and $CD34^+$ cells. The blocking agents used in this method are preferably selected from those blocking agents described in the discussion of the first aspect of the invention. As in the method previously described herein, this agent may be administered alone or in conjunction with an agent that stimulates proliferation of stem cells. The proliferation stimulating agent optionally used in this method is preferably selected from those proliferation stimulating agents described in the discussion of the second aspect of the invention. Peripheral blood is then collected by leukapheresis. Stem cells are then enriched from the collected peripheral blood by immunoadsorption using anti-CD34 antibodies. Such stem cell enrichment is known in the art and has been described, for example, by Berenson, Transplantation Proceedings 24:3032–3034 (1992) and the references cited therein. Optionally, the enriched stem cells are then expanded ex vivo by culturing them in the presence of agents that stimulate proliferation of stem cells. This ex vivo expansion can be carried out using, alone or in combination, any of the proliferation stimulating agents described in the discussion of the second aspect of the invention. Such ex vivo expansion of $CD34^+$ cells from peripheral blood is known in the art and has been described, for example, by Bruggar et al., Blood 81:2579–2584 (1993). The enriched and optionally expanded stem cells are then infected with an amphotrophic retroviral vector, or other appropriate vector, that expresses a gene that ameliorates the genetic or acquired disease. optionally, the vector may also carry an expressed selectable marker, in which case successfully transduced cells may be selected for the presence of the selectable marker. The transduced and optionally selected stem cells are then returned to the patient's circulating blood and allowed to engraft themselves into the bone marrow. The usefulness of approaches to using stem cells from peripheral blood for retroviral-mediated gene transfer and subsequent transplantation into a patient is recognized in the art and has been described, for example, by Bragni et al., Blood 80:1418–1422 (1992). The present method according to the invention provides an improvement in the transplantation of stem cells from peripheral blood by increasing the concentration of such stem cells in the peripheral blood, thereby greatly improving the likelihood of success of the retroviral transfection and subsequent transplantation and allows for repeated administration of genetically engineered cells in patients with partially ablative regimens and receiving agents that promote proliferation of transduced cells. Such stem cell enrichment is known in the art and has been described, for example, by Berenson, Transplantation Proceedings 24:3032–3034 (1992) and the references cited therein.

The instant invention is useful for many purposes. The methods of peripheralizing hematopoietic stem cells or $CD34^+$ cells is of value in scientific research dedicated to understanding the molecular interactions and molecular signals involved in the homing of these cells to bone marrow, as well as their trafficking in response to certain infections and trauma. This invention also provides sources of peripheral blood that is enriched in $CD34^+$ and hematopoietic stem cells, thus making the methods of the invention useful for therapeutic applications involving autologous transplantation of these cell types following chemotherapy or radiotherapy or in the course of gene therapy. The present invention provides many advantages over the current exclusively cytokine-based techniques. For example, peripheralization can be obtained without risk of cytokine-induced cell differentiation of normal cells or proliferation of contaminating leukemia cells and can be combined with cytotoxic agents. In addition, in the method of the invention, the timing of the peak of progenitors in peripheral blood is consistently between about 24 and about 72 hours from first injection of antibody, thus making the most beneficial timing for leukapheresis more predictable.

The efficacy of specific embodiments of methods according to both aspects of the instant invention is demonstrated in the examples. According to the first aspect of the invention, monoclonal antibodies against VLA-4 were administered to both macaques and a baboon. These antibodies, mouse monoclonal HP1/2, have previously been described by Pulido et al., J. Biol. Chem. 266:10241 (1991), and are known to block VLA-4 antigen on various cell surfaces. In the present case, administration of these antibodies resulted in as much as a 80-fold increase (average of 40-fold) in CFU-GM present in peripheral blood. The well known CFU-GM assay is the most widely used measure of the hematopoietic progenitor viability of a PBSC harvest and correlates well with per cent $CD34^+$ cells present in peripheral blood (see Craig et al., Blood Reviews 6:59–67 (1992)). Thus, these results demonstrate that, in a primate, administering a blocking agent of VLA-4 antigen on the surface of hematopoietic stem cells and $CD34^+$ cells results in peripheralization of the hematopoietic stem cells and $CD34^+$ cells. These results should be applicable to humans as well.

According to the second aspect of the invention, monoclonal antibodies against VLA-4 were administered to a macaque after five days of treatment with G-CSF. It is well known that G-CSF can stimulate hematopoietic stem cells and $CD34^+$ cells in vivo (see Metcalf, Nature 339:27–30 (1989)). G-CSF alone caused an increase in CFU-GM present in peripheral blood by days 4 and 5 of treatment. After discontinuation of G-CSF treatment and commencement of treatment with anti-VLA-4 antibodies, the number of CFU-GM in peripheral blood increased even more dramatically. It will be recognized by those skilled in the art that G-CSF alone does not cause the type of post-treatment increases in CFU-GM that were observed in the present case, as confirmed by a control experiment using G-CSF alone. Thus, these results demonstrate that, in a primate, administering a blocking agent of VLA-4 antigen on the surface of hematopoietic stem cells and $CD34^+$ cells in combination with administering a stimulating agent for proliferation of these cells has a synergistic effect. There is no reason to believe that these results will not apply equally well to humans.

Although not wishing to be bound by theory, Applicant believes that administering a blocking agent of VLA-4 antigens on the surface of hematopoietic stem cells and $CD34^+$ cells causes peripheralization of these cells by mediating release of the cells from the marrow environment via disruption of interactions between VLA-4 and its microenvironmental ligands, such as fibronectin and/or VCAM-1 on stromal cells or in the ECM. Administering stimulating agents of hematopoietic stem cell and $CD34^+$ cell proliferation is believed to cause peripheralization at least in part via sheer increase in the numbers of these cells. Thus, it is believed that administering a blocking agent of VLA-4 antigens in combination with a stimulating agent of stem cell proliferation effect peripheralization by complementary mechanisms. The observed synergisitic effect between anti-VLA-4 antibodies and G-CSF supports this interpretation. In addition, the observed synergistic effect between anti-VLA-4 antibodies and 5-fluorouracil further confirms this interpretation. Since these mechanisms appear to be complementary, the observed synergistic effect should be observed, regardless of whether administration of the blocking agent of VLA-4 antigens and stimulation of proliferation are carried out concomitantly or in sequence.

The following examples are intended to further illustrate certain preferred embodiments of the invention and are not intended to be limiting in nature.

EXAMPLE 1

Peripheralization Of Stem Cells Using An Anti-VLA-4 Antibody

Figure 1B:
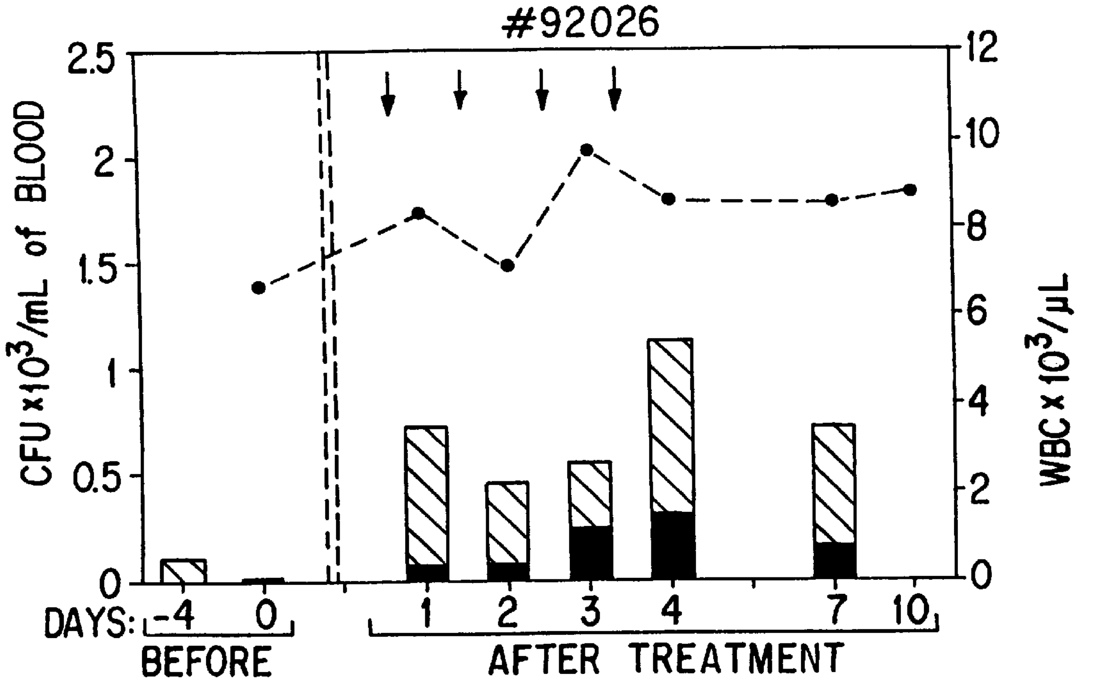
FIG. 1B is a profile of total white blood cells and CFU in peripheral blood of a baboon after treatment with anti-VLA-4 antibodies.
Figure 1C:
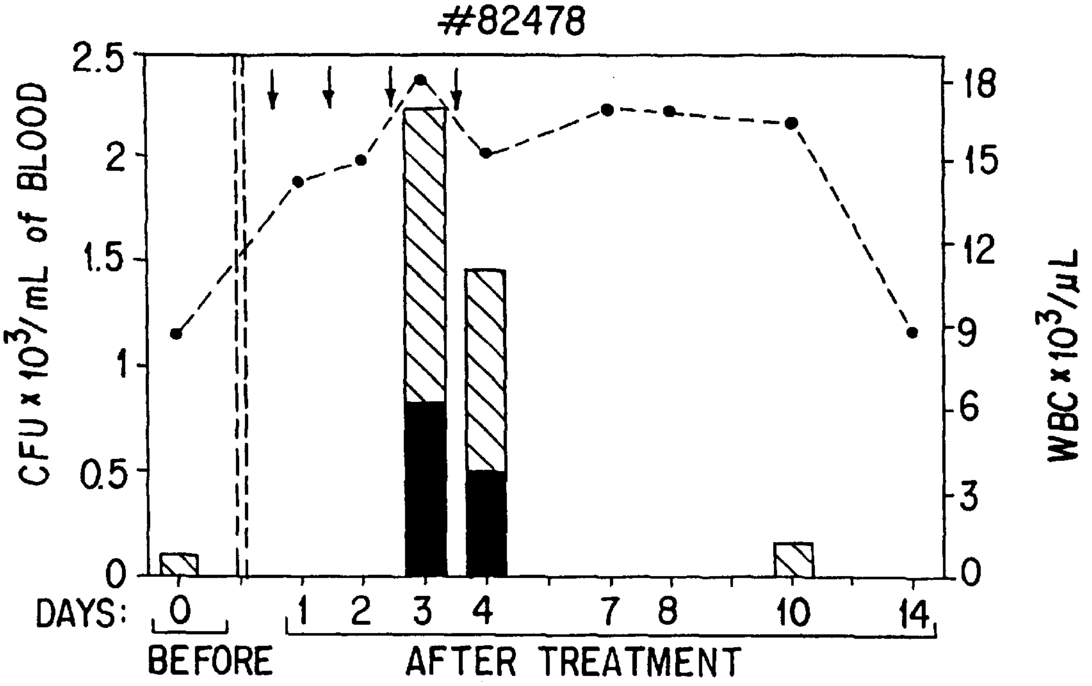
FIG. 1C is a profile of total white blood cells and CFU in peripheral blood of a macaque after treatment with anti-VLA-4 antibodies.

Three macaques and one baboon were injected intravenously with anti-VLA-4 mouse monoclonal antibody HP1/2 (1 mg/kg body weight/day) for four consecutive days. At various time points during and after completion of treatment, peripheral blood was collected and mononuclear cells were collected using a conventional Ficoll-Hypaque separation procedure. Total white blood cells were calculated from the number of mononuclear cells recovered per milliliter of blood. CFU-GM and BFUe were determined according to conventional assays (see, e.g., Papayannopoulou et al., Science 224:617 (1984)). The results of these studies are shown for two macaques (panels A and C) and one baboon (panel B) in FIG. 1. These results demonstrate that treatment of these primates with an anti-VLA-4 monoclonal antibody causes a small increase (up to 2-fold) in the total white blood cell count, peaking at about 2 to 4 days after beginning of treatment. More importantly, the total CFU-GM per ml blood increased much more dramatically (about 40-fold), also peaking at about 2 to 4 days after beginning of treatment. In another macaque, a CFU-GM increase of about 8-fold was observed after a single injection of antibody (data not shown). Given the well established use of the CFU-GM assay to measure the repopulating potential of hematopoietic progenitors and the correlation between CFU-GM and percentage $CD34^+$, these results establish that the anti-VLA-4 antibodies cause peripheralization of stem cells.

EXAMPLE 2

Failure of CD18 Blocking Agents to Cause Peripheralization of Stem Cells

Figure 2:
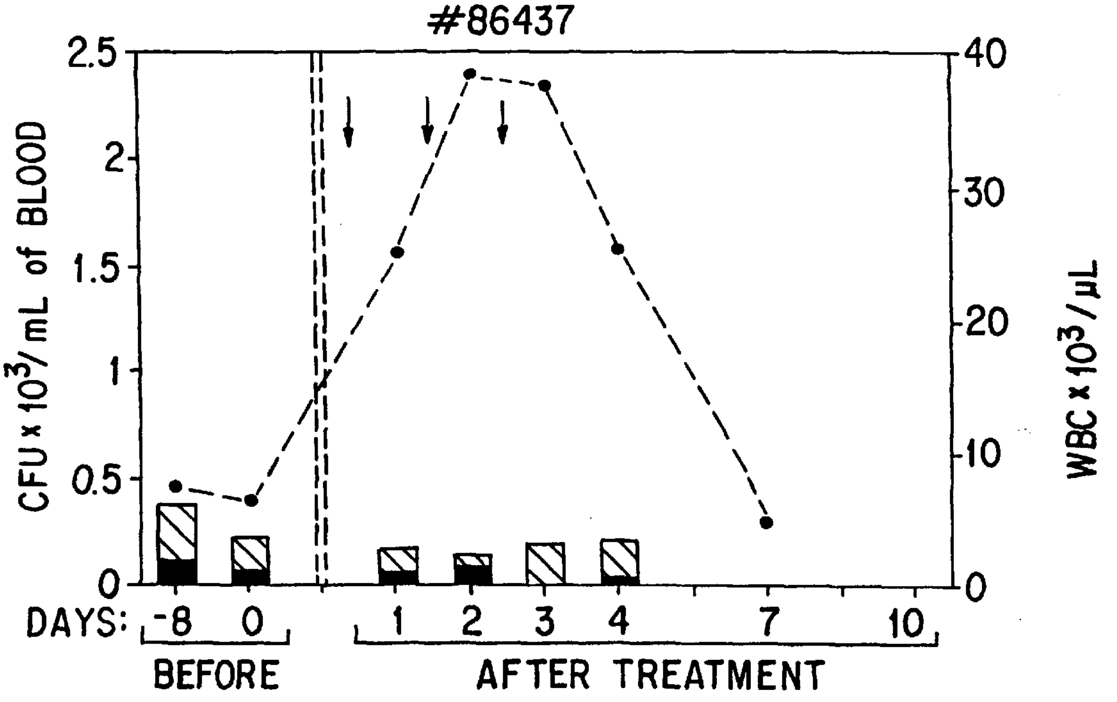
FIG. 2 is a profile of total white blood cells and CFU in peripheral blood before and after treatment of an animal with the and-CD18 monoclonal antibody 60.3. All symbols are as defined above.

The antigen CD18 is present on stem cells and is widely believed to be important in interactions involving stem cells. To test whether blocking agents for CD18 could cause peripheralization of stem cells, another macaque was treated with a monoclonal antibody against CD18. Antibody was delivered by intravenous injection for three days at a dosage of 2mg/kg of body weight/day. The results of this control experiment are shown in FIG. 2. Total white blood cell counts did increase with this treatment, consistent with previous experiments with rabbits. However, total GFU-GM showed no increase after treatment with anti-CD18 monoclonal antibodies. Thus, even though CD18 is widely believed to be important in interactions involving stem cells, blocking agents of CD18 do not lead to peripheralization of stem cells or progenitor cells. These results confirm that the peripheralization of stem cells observed upon treatment with anti-VLA-4 monoclonal antibody was indeed due to specific blocking of VLA-4.

EXAMPLE 3

Figure 3A:
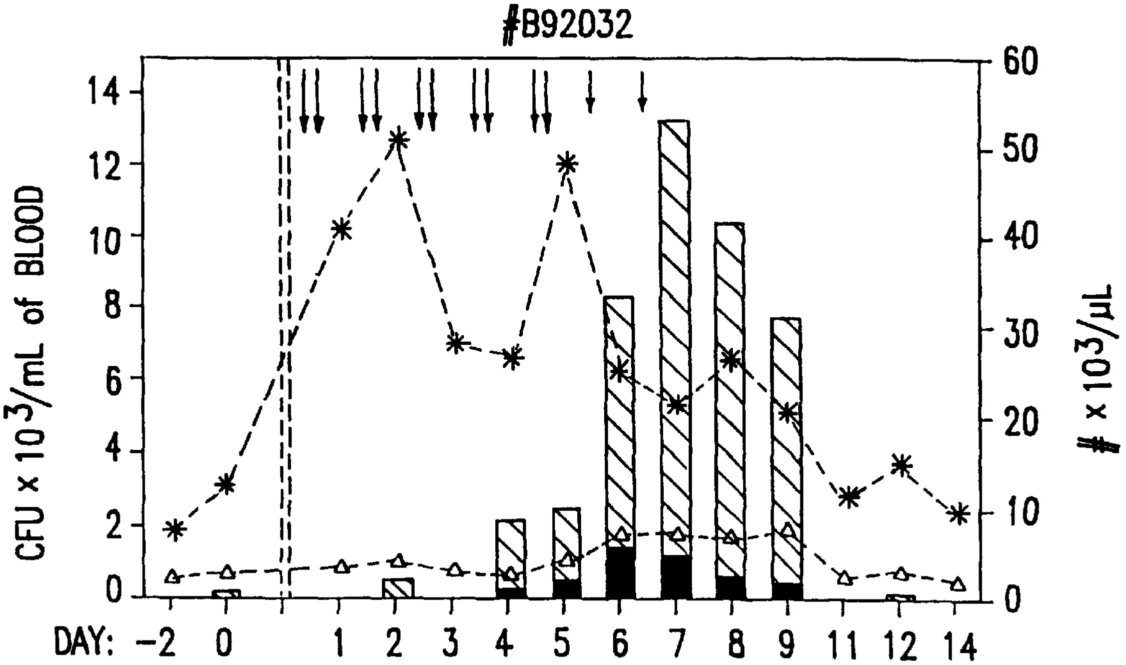
FIG. 3A is a profile of the results of combined treatment with G-CSF and anti-VLA-4 monoclonal antibody HP1/2. The symbols are as defined above, except that narrow downward-pointing arrows represent points of G-CSF administration, bold downward-pointing arrows represent points of antibody administration, and dotted line (with triangles) represent total lymphocyte counts.
Figure 3B:
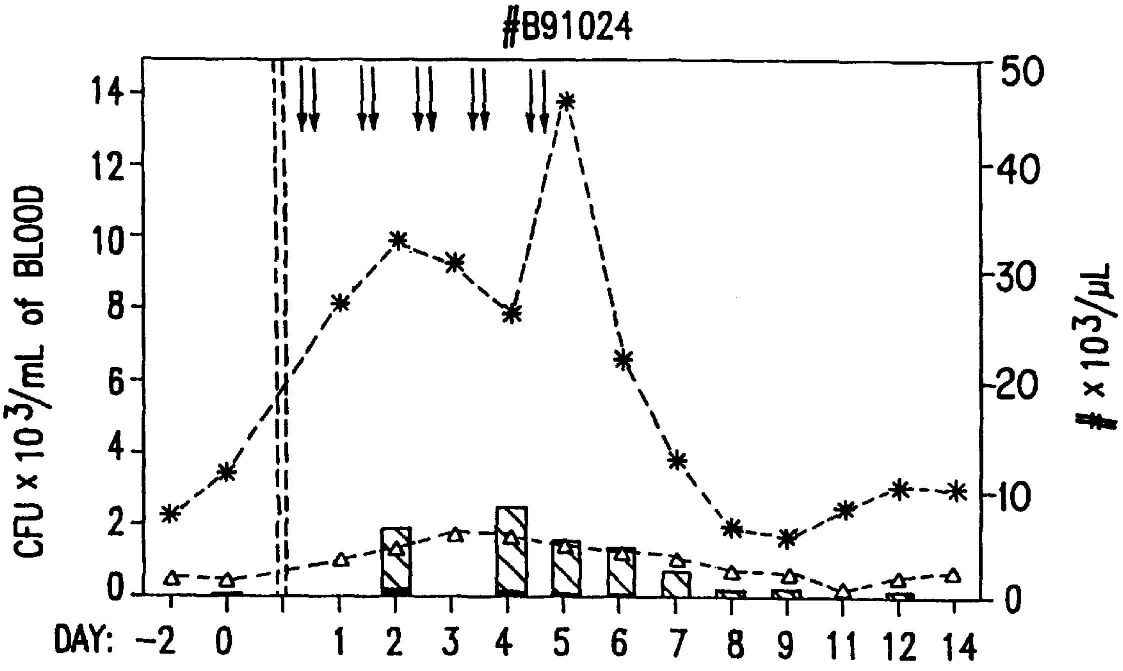
FIG. 3B is a profile of the results for a control animal treated with GCSF alone.

Synergistic Peripheralization Of Stem Cells Resulting From Treatment With Both Anti-VLA-4 Antibody In Combination With G-CSF A baboon was treated with recombinant human G-CSF twice daily for five consecutive days. Each G-CSF treatment consisted of intravenous injection of 15 micrograms G-CSF per kilogram of body weight. After the five days of G-CSF administration, the baboon received two injections, spaced one day apart, of anti-VLA-4 monoclonal antibody (HP1/2). Each injection contained 1 milligram antibody per kilogram body weight. Total white blood cells and CFU-GM were determined as described in Example 1. The results are shown in FIG. 3. As shown in panel A of that figure, G-CSF resulted in the expected increase in CFU-GM by days 4 and 5 of treatment, along with a marked increase in total white blood cells. Surprisingly, after the administration of anti-VLA-4 antibody beginning after the last day of a 5 day G-CSF treatment, yet another marked increase in CFU-GM was observed, this time without any increase in total white blood cells. This second increase resulted in about a six-fold improvement in the number of CFU-GM, relative to G-CSF alone. A control animal treated with G-CSF alone according to the same protocol showed a continuous decline in peripheral blood CFU after cessation of treatment (see FIG. 3, panel B). These results indicate that treatment with anti-VLA-4 antibody was responsible for this second increase in CFU-GM. Thus, combined treatment with anti-VLA-4 antibody and G-CSF results in a synergistic effect, causing far greater increases in CFU-GM than treatment by either G-CSF or anti-VLA-4 antibodies alone.

EXAMPLE 4

Figure 4A:
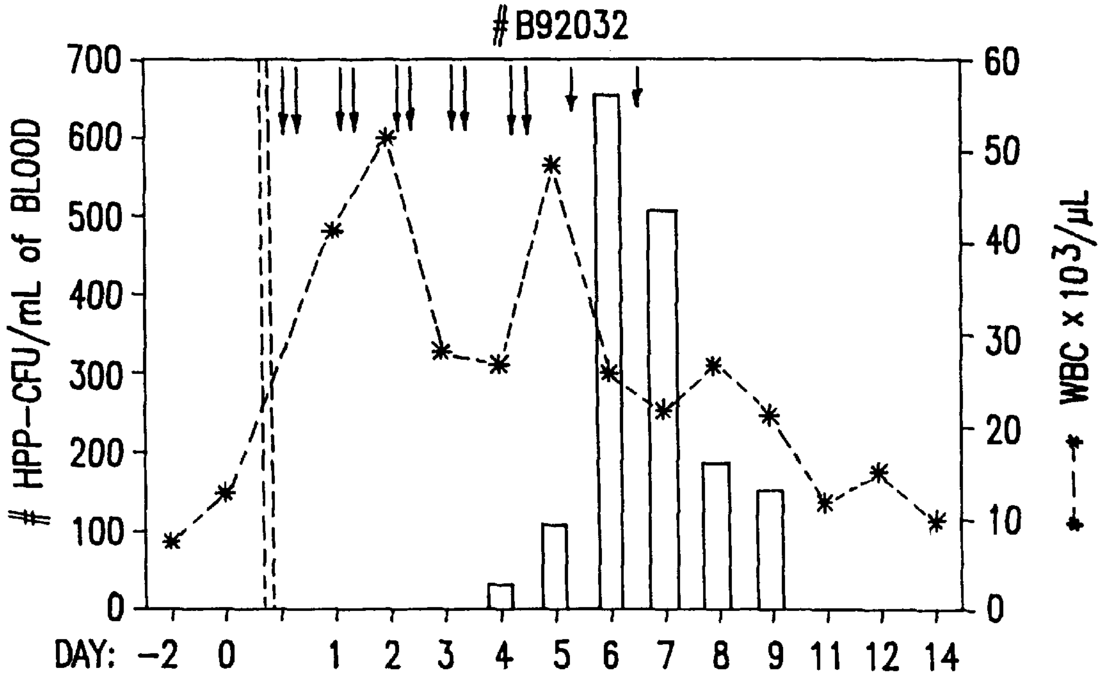
FIG. 4A shows high proliferative potential (HPP) progenitors (colonies over 0.5 mm in diameter of compact growth) resulting from combined treatment with GCSF and HP1/2 antibody.
Figure 4B:
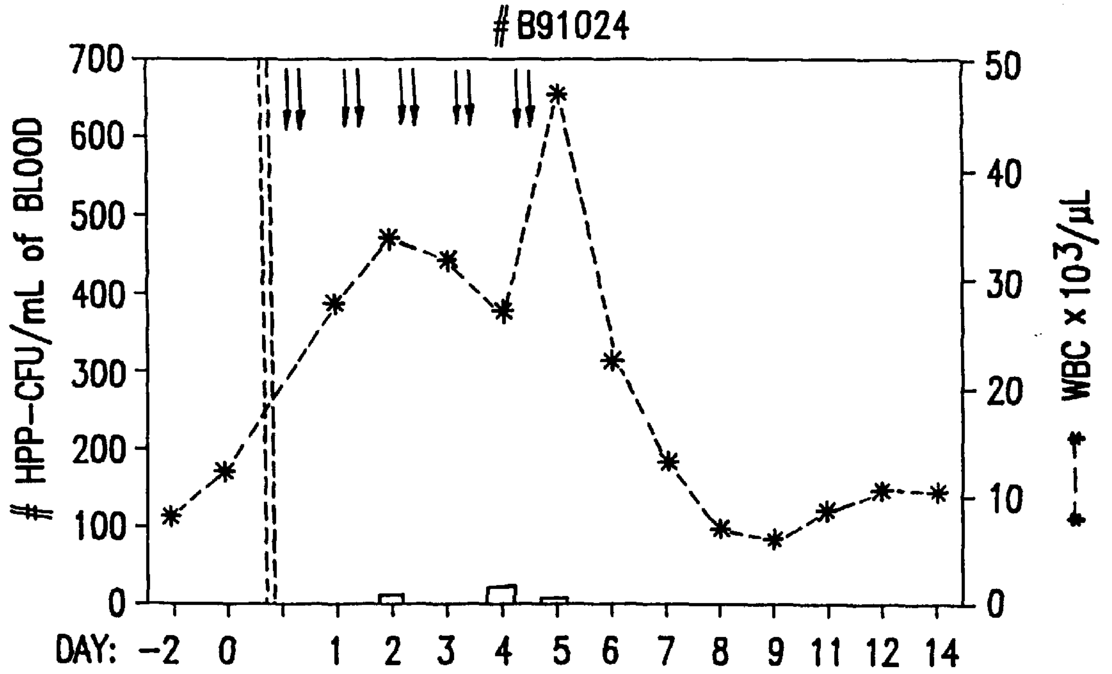
FIG. 4B is a profile of HPP progenitors resulting from treatment with GCSF alone. Symbols are as in FIG. 3.

Analysis Of High Proliferative Potential Cells In Peripheral Blood Following Combined Treatment With G-CSF And Anti-VLA-4 Antibody In the experiments described in Example 3, high proliferative potential (HPP) cells were also counted. HPP cells are cells that give rise to colonies that are macroscopically visible, over 0.5 mm in diameter with dense, compact growth on the analysis grid. Presence of these cells is associated with greater repopulation capacity and such cells are believed to be earlier progenitors. The results are shown in FIG. 4. The observed disparity in peripheral blood HPP cells between G-CSF treatment alone and G-CSF treatment in combination with anti-VLA-4 antibodies is even greater than the disparity observed for CFU-GM. These results suggest that the combined treatment not only produces more progenitors, but also produces earlier progenitors having potentially greater repopulation capacity.

EXAMPLE 5

Figure 6A:
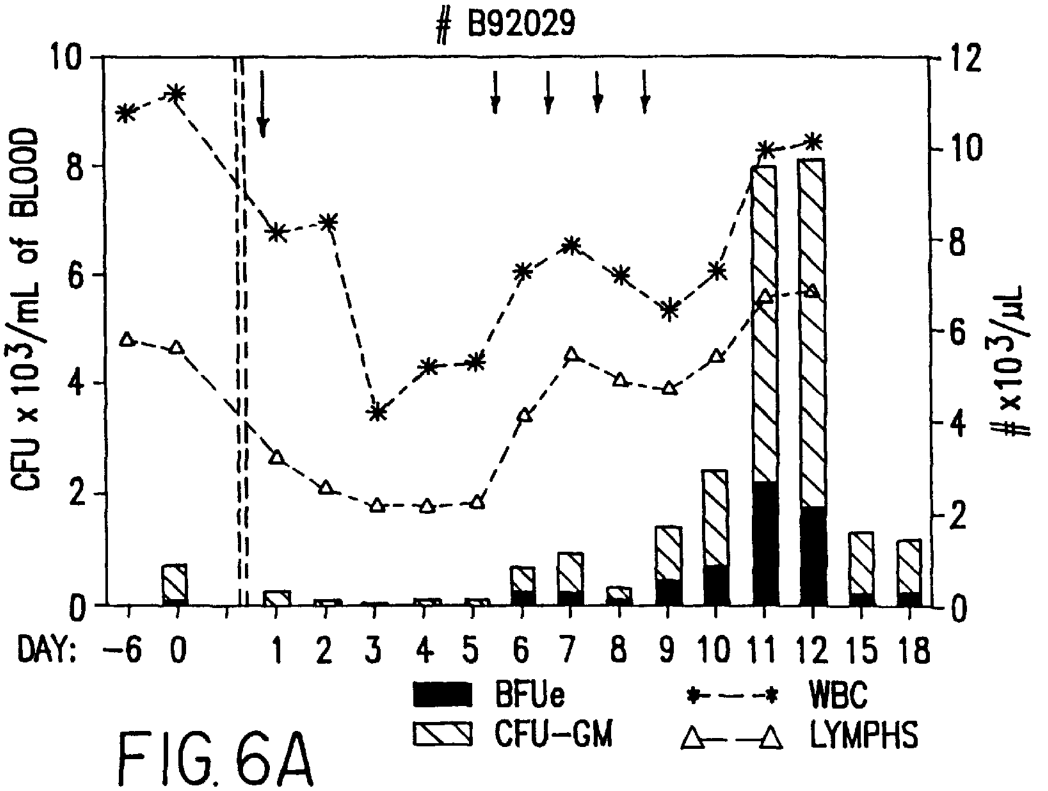
FIG. 6A is a profile of the results of combined treatment with 5-fluorouracil and anti-VLA-4 murine monoclonal antibody HP1/2. Symbols are as described for FIG. 3.
Figure 6B:
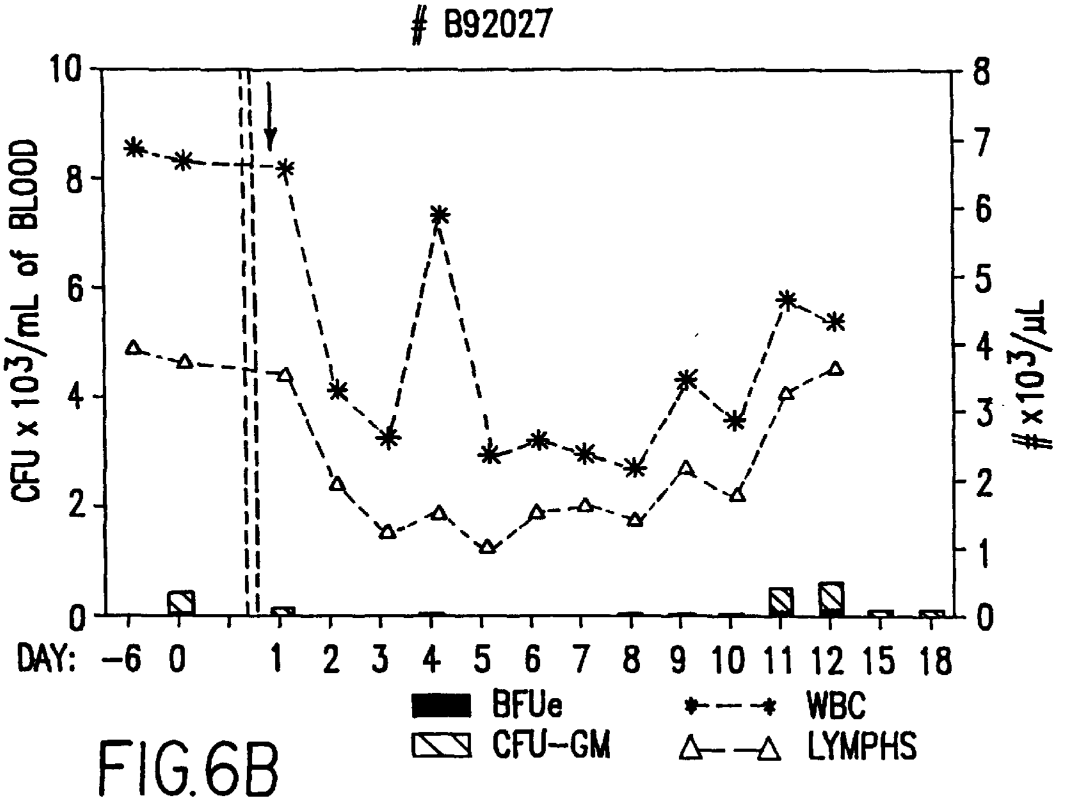
FIG. 6B is a profile of the results of 5-fluorouracil treatment alone.

Synergistic Peripheralization Of Stem Cells Resulting From Treatment With Anti-VLA-4 Antibody In Combination With 5-Fluorouracil A baboon was treated with the chemotherapeutic agent 5-fluorouracil at a dosage of 100 mg per kilogram body weight. Beginning five days later, the baboon received four injections, spaced one day apart, of anti-VLA-4 monoclonal antibody (HP1/2). Each injection contained one milligram antibody per kilogram body weight. Total white blood cells and CFU-GM were determined as described in Example 1. The results are shown in FIG. 6. As shown in panel B of that figure, 5-fluorouracil alone produced a modest increase in CFU-GM at days 11 and 12. Administration of anti-VLA-4 antibody after the 5-fluorouracil, however, resulted in a dramatic further increase in CFU-GM, an increase of greater than ten times that produced by 5-fluorouracil alone. These results indicate that combined treatment with anti-VLA-4 antibody and 5-fluorouracil produces a synergistric effect, causing far greater increases in CFU-GM than treatment with either agent alone. Moreover, when taken together with the G-CSF/anti-VLA-4 antibody results, these results strongly support the theory that the observed synergism results from stimulation of proliferation of progenitors by one agent and release of the progenitors from the marrow by another. Thus, these results strongly suggest that such a synergistic effect can be produced by any agent that can stimulate proliferation, in conjunction with any agent that can bring about release from the marrow.

EXAMPLE 6

Preparation Of A Humanized Anti-VLA-4 Antibody

The complementarity determining regions (CDRs) of the light and heavy chains of the-anti-VLA-4 monoclonal antibody HP1/2 were determined according to the sequence alignment approach of Kabat et al., 1991, 5th Ed., 4 vol., Sequences of Proteins of Immunological Interest, U.S. Department of Health and Human Services, NIH, U.S.A. The CDRs of murine HP1/2 $V_H$ correspond to the residues identified in the humanized $V_H$ sequences disclosed herein as amino acids 31–35 (CDR1), 50–66 (CDR2) and 99–110 (CDR3), which respectively corresond to amino acids 31–35, 50–65 and 95–102 in the Kabat alignment. The CDRs of murine HP1/2 $V_K$ correspond to the residues identified in the humanized $V_K$ sequences disclosed herein as amino acids 24–34 (CDR1), 50–56 (CDR2) and 89–97 (CDR3), and to the same residues in the Kabat alignment. The Kabat NEWM framework was chosen to accept the heavy chain CDRs and the Kabat REI framework was chosen to accept the kappa chain CDRs. Transplantation of the CDRs into the human frameworks was achieved by using M13 mutagenesis vectors and synthetic oligonucleotides containing the HP1/2 CDR-encoding sequences flanked by short sequences derived from the frameworks. The $V_H$ mutagenesis vector, M13VHPCR1 contains the NEWM framework and has been described by Orlandi et al., Proc. Natl. Acad. Sci U.S.A. 86:3833–3837 (1989). The $V_K$ mutagenesis vector, M13VKPCR2 contains essentially the REI framework and is identical to the M13VKPCR1 vector described by Orlandi et al., except that there is a single amino acid change from Val to Glu in framework 4. Transplanted product was recovered by PCR and cloned into M13mp19 for sequencing. The transplanted $V_H$ sequence [SEQ. ID NO:3] is shown in FIG. 7, panel A. In addition to the CDR grafting, this product encodes the murine amino acids at positions 27–30 and an Arg to Asp change at position 94. The transplanted $V_K$ sequence [SEQ. ID NO:4] is shown in FIG. 7, panel B.

Additional modifications were introduced via the two step PCR-directed mutagenesis method of Ho et al., Gene 77:51–59 (1989). For the $V_H$ sequence, position 24 (Kabat numbering) was changed from Val to Ala and position 75 (Kabat numbering) was changed from Lys to Ser, then amino acid positions 27–30 and 94 were mutated back to the NEWM sequences. The final humanized $V_H$ sequence [SEQ. ID NO:5] is shown in FIG. 8, panel A. For the $V_K$ sequence, the same two step PCR-directed mutagenesis approach was used to introduce additional modifications. The final humanized $V_K$ sequence [SEQ. ID NO:6] is shown in FIG. 8, panel B.

The entire $V_H$ and $V_K$ regions of humanized HP1/2 were cloned into appropriate expression vectors. The appropriate human IgG1, IgG4 or kappa constant region was then added to the vector in appropraite reading frame with respect to the murine variable regions. The vectors were then cotransduced into YB2/0 ray myeloma cells (available from ATCC), which were then selected for the presence of both vectors. ELISA analysis of cell supernatants demonstrated that the humanized antibody produced by these cells was at least equipotent with murine HP1/2. The cell line expressing this humanized antibody was deposited with the ATCC on Nov. 3, 1992 and given accession number CRL 11175.

EXAMPLE 7

Figure 9:
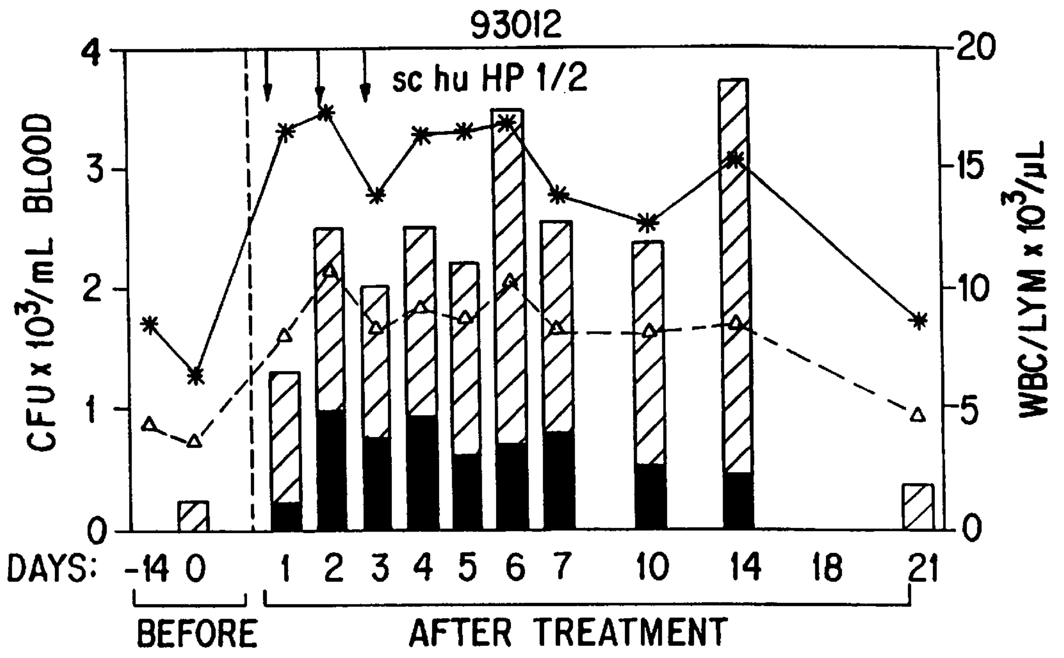
FIG. 9. is a profile of the results of treatment with humanized anti-VLA-4 antibody hHP1/2. Symbols are as described for FIG. 3.
Figure 10:
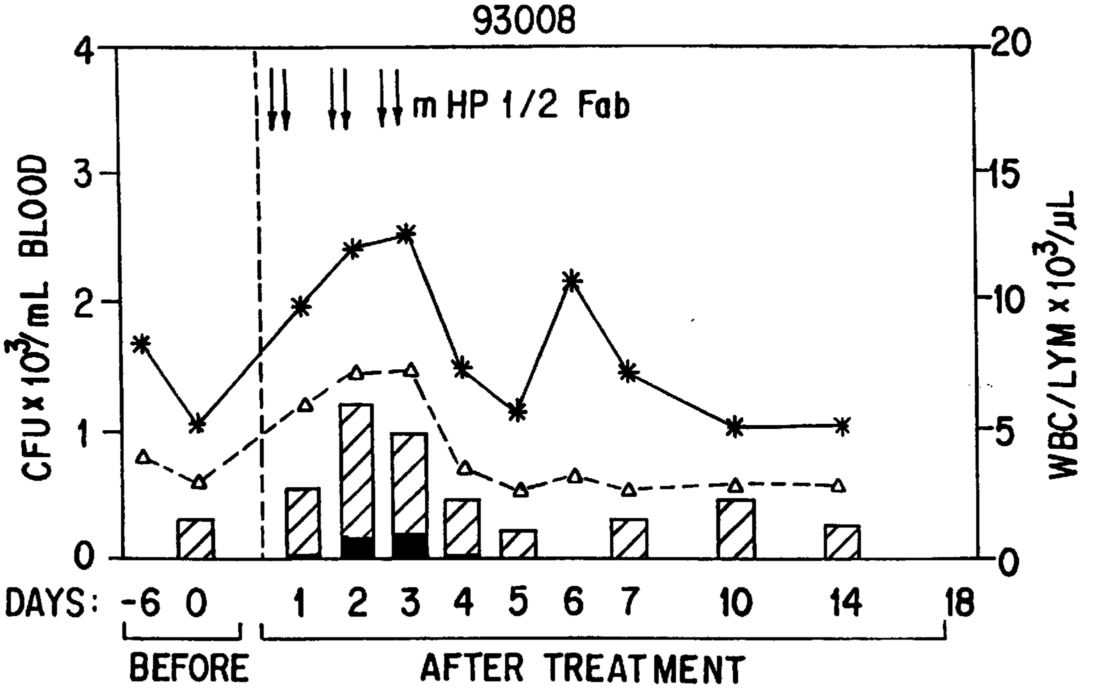
FIG. 10 is a profile of the results of treatment with murine Fab fragments of anti-VLA-4 antibody HP1/2. Symbols are as described for FIG. 3.

Peripheralization Of Stem Cells Resulting From Treatment With Humanized Anti-VLA-4 Antibody Humanized anti-VLA-4 antibodies prepared according to Example 6 were tested for peripheralizing stem cells. The baboon modelwas used again with three daily antibody injections. The results are shown in FIG. 9. As previously shown for murine antibody, the humanized anti-VLA-4 antibody produces a large increase in peripheralized CFU. Thus, humanized VLA-4 antibodies are capable of causing peripheralization of stem cells and progenitor cells in the same manner as the murine monoclonal antibody HP1/2. This result suggests that the humanized antibody may also be capable, like the monoclonal antibody, of acting synergistically in combination with G-CSF for peripheralizing stem cells.

EXAMPLE 8

Peripheralization Of Stem Cells Resulting From Treatment With Anti-VLA-4 Murine Fab Fragment Fab fragments from the murine antibodwere HP1/2 were tested for their ability to peripheralize stem cells and progenitor cells. The experiment was performed by administration of 1 mg/kg of Fab fragment twice daily for three days. In this instance, a modest effect (compared with humanized or monoclonal antibody) was observed, due to the rapid clearance of Fab fragments. Though modest, the observed characteristic BFU-e increase validates this result. This result demonstrates that anti-VLA-4 antibody Fab fragments are capable of causing peripheralization of stem cells and progenitor cells. This suggests that anti-VLA-4 Fab fragments may be capable of acting synergistically in combination with G-CSF for peripheralizing stem cells. In addition, since the Fab fragments are not known to have any effector function other than binging antigen, this result suggests that any blocking agent that can bind VLA-4 and thereby block its interaction with VCAM-1 will be capable of peripheralizing stem cells, and in doing so, of acting synergistically with factors that promote stem cell proliferation.

I claim:

1. A method of treating AIDS in a patient comprising the steps of:

(1) peripheralizing CD34+ cells by administering an anti-VLA-4 antibody which blocks the binding of VLA-4 antigen on the surface of said CD34+ cells to VCAM or fibronectin;

(2) collecting peripheral blood containing the CD34+ cells by leukapheresis;

(3) enriching the CD34+ cells by immunoadsorption using anti-CD34 antibodies;

(4) administering chemotherapy and/or radiotherapy to the patient; and (5) returning the enriched CD34+ cells to the patient's circulating blood.

2. The method according to claim 1, further comprising administering an anti-HIV agent to the patient prior to returning the enriched $CD34^+$ cells to the patient's circulating blood.

3. The method according to claim 1, further comprising the step of administering a stimulating agent of CD34+ cell proliferation in vivo prior to leukapheresis, said stimulating agent being 5-fluorouracil or a cytokine that stimulates hematopoietic cells to proliferated.

4. The method according to claim 1, further comprising the step of expanding the enriched $CD34^+$ cells ex vivo prior to returning the cells to the patient's circulating blood.

5. The method according to claim 2, further comprising the step of administering a stimulating agent of $CD34^+$ cell proliferation in vivo prior to leukapheresis.

6. The method according to claim 2, further comprising the step of expanding the enriched $CD34^+$ cells ex vivo prior to returning the cells to the patient's circulating blood.

7. The method according to claim 1, wherein the anti-VLA-4 antibody is selected from the group consisting of an antibody which is human, mouse/human chimeric, single chain, and humanized or Fab, Fab', F(ab')2 or F(v) fragments thereof.

8. The method according to claim 1, wherein at least a portion of the $CD34^+$ cells are hematopoietic stem cells.

9. The method according to claim 1, wherein the cytokine is selected from the group consisting of G-CSF, stem cell factor, GM-CSF, M-CSF, T-SCF, SCPF, IL-1, IL-2, IL-3, IL-4, IL-6 and IL-11.

10. The method according to claim 9, wherein the cytokine is G-CSF.

11. The method according to claim 3, wherein the stimulating agent is administered before administering the anti-VLA-4 antibody.

12. The method according to claim 3, wherein the anti-VLA-4 antibodies is administered simultaneously with the stimulating agent.

* * * * *

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
( A ) LENGTH: 360 base pairs
( B ) TYPE: nucleic acid
( C ) STRANDEDNESS: single
( D ) TOPOLOGY: linear (xi) SEQUENCE DESCRIPTION: SEQ ID NO:1:

```
GTCAAACTGC AGCAGTCTGG GGCAGAGCTT GTGAAGCCAG GGGCCTCAGT CAAGTTGTCC    60
TGCACAGCTT CTGGCTTCAA CATTAAAGAC ACCTATATGC ACTGGGTGAA GCAGAGGCCT   120
GAACAGGGCC TGGAGTGGAT TGGAAGGATT GATCCTGCGA GTGGCGATAC TAAATATGAC   180
CCGAAGTTCC AGGTCAAGGC CACTATTACA GCGGACACGT CCTCCAACAC AGCCTGGCTG   240
CAGCTCAGCA GCCTGACATC TGAGGACACT GCCGTCTACT ACTGTGCAGA CGGAATGTGG   300
GTATCAACGG GATATGCTCT GGACTTCTGG GGCCAAGGGA CCACGGTCAC CGTCTCCTCA   360
```

(2) INFORMATION FOR SEQ ID NO:2:

(i) SEQUENCE CHARACTERISTICS:
(A) LENGTH: 318 base pairs
(B) TYPE: nucleic acid
(C) STRANDEDNESS: single
(D) TOPOLOGY: linear (xi) SEQUENCE DESCRIPTION: SEQ ID NO:2:

```
AGTATTGTGA TGACCCAGAC TCCCAAATTC CTGCTTGTTT CAGCAGGAGA CAGGGTTACC    60
ATAACCTGCA AGGCCAGTCA GAGTGTGACT AATGATGTAG CTTGGTACCA ACAGAAGCCA   120
GGGCAGTCTC CTAAACTGCT GATATATTAT GCATCCAATC GCTACACTGG AGTCCCTGAT   180
CGCTTCACTG GCAGTGGATA TGGGACGGAT TTCACTTTCA CCATCAGCAC TGTGCAGGCT   240
GAAGACCTGG CAGTTTATTT CTGTCAGCAG GATTATAGCT CTCCGTACAC GTTCGGAGGG   300
GGGACCAAGC TGGAGATC                                                 318
```

(2) INFORMATION FOR SEQ ID NO:3:

(i) SEQUENCE CHARACTERISTICS:
(A) LENGTH: 429 base pairs
(B) TYPE: nucleic acid
(C) STRANDEDNESS: single
(D) TOPOLOGY: linear (ix) FEATURE:
(A) NAME/KEY: sig_peptide
(B) LOCATION: 1..57

(ix) FEATURE:
(A) NAME/KEY: mat_peptide
(B) LOCATION: 58..429

(ix) FEATURE:
(A) NAME/KEY: CDS
(B) LOCATION: 1..429

(ix) FEATURE:
(A) NAME/KEY: misc_feature
(B) LOCATION: 1
(D) OTHER INFORMATION: /note= "pMDR1019 insert: Stage 1 heavy chain variable region"

(xi) SEQUENCE DESCRIPTION: SEQ ID NO:3:

```
ATG GAC TGG ACC TGG AGG GTC TTC TGC TTG CTG GCT GTA GCA CCA GGT    48
Met Asp Trp Thr Trp Arg Val Phe Cys Leu Leu Ala Val Ala Pro Gly
-19             -15                 -10                  -5

GCC CAC TCC CAG GTC CAA CTG CAG GAG AGC GGT CCA GGT CTT GTG AGA    96
Ala His Ser Gln Val Gln Leu Gln Glu Ser Gly Pro Gly Leu Val Arg
              1                   5                  10

CCT AGC CAG ACC CTG AGC CTG ACC TGC ACC GTG TCT GGC TTC AAC ATT   144
Pro Ser Gln Thr Leu Ser Leu Thr Cys Thr Val Ser Gly Phe Asn Ile
     15                  20                  25

AAA GAC ACC TAT ATG CAC TGG GTG AGA CAG CCA CCT GGA CGA GGT CTT   192
Lys Asp Thr Tyr Met His Trp Val Arg Gln Pro Pro Gly Arg Gly Leu
```

-continued

```
30                        35                        40                        45

GAG TGG ATT GGA AGG ATT GAT CCT GCG AGT GGC GAT ACT AAA TAT GAC     240
Glu Trp Ile Gly Arg Ile Asp Pro Ala Ser Gly Asp Thr Lys Tyr Asp
                 50                  55                  60

CCG AAG TTC CAG GTC AGA GTG ACA ATG CTG GTA GAC ACC AGC AAG AAC     288
Pro Lys Phe Gln Val Arg Val Thr Met Leu Val Asp Thr Ser Lys Asn
             65                  70                  75

CAG TTC AGC CTG AGA CTC AGC AGC GTG ACA GCC GCC GAC ACC GCG GTC     336
Gln Phe Ser Leu Arg Leu Ser Ser Val Thr Ala Ala Asp Thr Ala Val
         80                  85                  90

TAT TAT TGT GCA GAC GGA ATG TGG GTA TCA ACG GGA TAT GCT CTG GAC     384
Tyr Tyr Cys Ala Asp Gly Met Trp Val Ser Thr Gly Tyr Ala Leu Asp
     95                 100                 105

TTC TGG GGC CAA GGG ACC ACG GTC ACC GTC TCC TCA GGT GAG TCC         429
Phe Trp Gly Gln Gly Thr Thr Val Thr Val Ser Ser Gly Glu Ser
110                 115                 120
```

( 2 ) INFORMATION FOR SEQ ID NO:4:

( i ) SEQUENCE CHARACTERISTICS:
( A ) LENGTH: 143 amino acids
( B ) TYPE: amino acid
( D ) TOPOLOGY: linear ( i i ) MOLECULE TYPE: protein ( x i ) SEQUENCE DESCRIPTION: SEQ ID NO:4:

```
Met Asp Trp Thr Trp Arg Val Phe Cys Leu Leu Ala Val Ala Pro Gly
-19             -15                 -10                  -5

Ala His Ser Gln Val Gln Leu Gln Glu Ser Gly Pro Gly Leu Val Arg
              1                   5                  10

Pro Ser Gln Thr Leu Ser Leu Thr Cys Thr Val Ser Gly Phe Asn Ile
     15                  20                  25

Lys Asp Thr Tyr Met His Trp Val Arg Gln Pro Pro Gly Arg Gly Leu
 30                  35                  40                  45

Glu Trp Ile Gly Arg Ile Asp Pro Ala Ser Gly Asp Thr Lys Tyr Asp
                 50                  55                  60

Pro Lys Phe Gln Val Arg Val Thr Met Leu Val Asp Thr Ser Lys Asn
             65                  70                  75

Gln Phe Ser Leu Arg Leu Ser Ser Val Thr Ala Ala Asp Thr Ala Val
         80                  85                  90

Tyr Tyr Cys Ala Asp Gly Met Trp Val Ser Thr Gly Tyr Ala Leu Asp
     95                 100                 105

Phe Trp Gly Gln Gly Thr Thr Val Thr Val Ser Ser Gly Glu Ser
110                 115                 120
```

( 2 ) INFORMATION FOR SEQ ID NO:5:

( i ) SEQUENCE CHARACTERISTICS:
( A ) LENGTH: 386 base pairs
( B ) TYPE: nucleic acid
( C ) STRANDEDNESS: single
( D ) TOPOLOGY: linear ( i x ) FEATURE:
( A ) NAME/KEY: sig_peptide
( B ) LOCATION: 1..57

( i x ) FEATURE:
( A ) NAME/KEY: mat_peptide
( B ) LOCATION: 58..384

( i x ) FEATURE:
( A ) NAME/KEY: CDS

-continued ( B ) LOCATION: 1..384

( i x ) FEATURE:
( A ) NAME/KEY: misc_feature
( B ) LOCATION: 1
( D ) OTHER INFORMATION: /note= "pBag190 insert: VK1 (DQL) light chain variable region"

( x i ) SEQUENCE DESCRIPTION: SEQ ID NO:5:

ATG GGT TGG TCC TGC ATC ATC CTG TTC CTG GTT GCT ACC GCT ACC GGT 48
Met Gly Trp Ser Cys Ile Ile Leu Phe Leu Val Ala Thr Ala Thr Gly
-19 -15 -10 -5

GTT CAC TCC GAC ATC CAG CTG ACC CAG AGC CCA AGC AGC CTG AGC GCC 96
Val His Ser Asp Ile Gln Leu Thr Gln Ser Pro Ser Ser Leu Ser Ala
1 5 10

AGC GTG GGT GAC AGA GTG ACC ATC ACC TGT AAG GCC AGT CAG AGT GTG 144
Ser Val Gly Asp Arg Val Thr Ile Thr Cys Lys Ala Ser Gln Ser Val
15 20 25

ACT AAT GAT GTA GCT TGG TAC CAG CAG AAG CCA GGT AAG GCT CCA AAG 192
Thr Asn Asp Val Ala Trp Tyr Gln Gln Lys Pro Gly Lys Ala Pro Lys
30 35 40 45

CTG CTG ATC TAC TAT GCA TCC AAT CGC TAC ACT GGT GTG CCA AGC AGA 240
Leu Leu Ile Tyr Tyr Ala Ser Asn Arg Tyr Thr Gly Val Pro Ser Arg
50 55 60

TTC AGC GGT AGC GGT AGC GGT ACC GAC TTC ACC TTC ACC ATC AGC AGC 288
Phe Ser Gly Ser Gly Ser Gly Thr Asp Phe Thr Phe Thr Ile Ser Ser
65 70 75

CTC CAG CCA GAG GAC ATC GCC ACC TAC TAC TGC CAG CAG GAT TAT AGC 336
Leu Gln Pro Glu Asp Ile Ala Thr Tyr Tyr Cys Gln Gln Asp Tyr Ser
80 85 90

TCT CCG TAC ACG TTC GGC CAA GGG ACC AAG GTG GAA ATC AAA CGT AAG 384
Ser Pro Tyr Thr Phe Gly Gln Gly Thr Lys Val Glu Ile Lys Arg Lys
95 100 105

TG 386

( 2 ) INFORMATION FOR SEQ ID NO:6:

( i ) SEQUENCE CHARACTERISTICS:
( A ) LENGTH: 128 amino acids
( B ) TYPE: amino acid
( D ) TOPOLOGY: linear ( i i ) MOLECULE TYPE: protein ( x i ) SEQUENCE DESCRIPTION: SEQ ID NO:6:

Met Gly Trp Ser Cys Ile Ile Leu Phe Leu Val Ala Thr Ala Thr Gly
-19 -15 -10 -5

Val His Ser Asp Ile Gln Leu Thr Gln Ser Pro Ser Ser Leu Ser Ala
1 5 10

Ser Val Gly Asp Arg Val Thr Ile Thr Cys Lys Ala Ser Gln Ser Val
15 20 25

Thr Asn Asp Val Ala Trp Tyr Gln Gln Lys Pro Gly Lys Ala Pro Lys
30 35 40 45

Leu Leu Ile Tyr Tyr Ala Ser Asn Arg Tyr Thr Gly Val Pro Ser Arg
50 55 60

Phe Ser Gly Ser Gly Ser Gly Thr Asp Phe Thr Phe Thr Ile Ser Ser
65 70 75

Leu Gln Pro Glu Asp Ile Ala Thr Tyr Tyr Cys Gln Gln Asp Tyr Ser
80 85 90

Ser Pro Tyr Thr Phe Gly Gln Gly Thr Lys Val Glu Ile Lys Arg Lys
95 100 105

(2) INFORMATION FOR SEQ ID NO:7:

(i) SEQUENCE CHARACTERISTICS:
(A) LENGTH: 429 base pairs
(B) TYPE: nucleic acid
(C) STRANDEDNESS: single
(D) TOPOLOGY: linear (ix) FEATURE:
(A) NAME/KEY: sig_peptide
(B) LOCATION: 1..57

(ix) FEATURE:
(A) NAME/KEY: mat_peptide
(B) LOCATION: 58..429

(ix) FEATURE:
(A) NAME/KEY: CDS
(B) LOCATION: 1..429

(ix) FEATURE:
(A) NAME/KEY: misc_feature
(B) LOCATION: 1
(D) OTHER INFORMATION: /note= "pBAG195 insert: AS heavy chain variable region"

(xi) SEQUENCE DESCRIPTION: SEQ ID NO:7:

```
ATG GAC TGG ACC TGG AGG GTC TTC TGC TTG CTG GCT GTA GCA CCA GGT      48
Met Asp Trp Thr Trp Arg Val Phe Cys Leu Leu Ala Val Ala Pro Gly
-19             -15                 -10                 -5

GCC CAC TCC CAG GTC CAA CTG CAG GAG AGC GGT CCA GGT CTT GTG AGA      96
Ala His Ser Gln Val Gln Leu Gln Glu Ser Gly Pro Gly Leu Val Arg
              1                   5                  10

CCT AGC CAG ACC CTG AGC CTG ACC TGC ACC GCG TCT GGC TTC AAC ATT     144
Pro Ser Gln Thr Leu Ser Leu Thr Cys Thr Ala Ser Gly Phe Asn Ile
     15                  20                  25

AAA GAC ACC TAT ATG CAC TGG GTG AGA CAG CCA CCT GGA CGA GGT CTT     192
Lys Asp Thr Tyr Met His Trp Val Arg Gln Pro Pro Gly Arg Gly Leu
 30                  35                  40                  45

GAG TGG ATT GGA AGG ATT GAT CCT GCG AGT GGC GAT ACT AAA TAT GAC     240
Glu Trp Ile Gly Arg Ile Asp Pro Ala Ser Gly Asp Thr Lys Tyr Asp
                 50                  55                  60

CCG AAG TTC CAG GTC AGA GTG ACA ATG CTG GTA GAC ACC AGC AGC AAC     288
Pro Lys Phe Gln Val Arg Val Thr Met Leu Val Asp Thr Ser Ser Asn
             65                  70                  75

CAG TTC AGC CTG AGA CTC AGC AGC GTG ACA GCC GCC GAC ACC GCG GTC     336
Gln Phe Ser Leu Arg Leu Ser Ser Val Thr Ala Ala Asp Thr Ala Val
         80                  85                  90

TAT TAT TGT GCA GAC GGA ATG TGG GTA TCA ACG GGA TAT GCT CTG GAC     384
Tyr Tyr Cys Ala Asp Gly Met Trp Val Ser Thr Gly Tyr Ala Leu Asp
     95                 100                 105

TTC TGG GGC CAA GGG ACC ACG GTC ACC GTC TCC TCA GGT GAG TCC         429
Phe Trp Gly Gln Gly Thr Thr Val Thr Val Ser Ser Gly Glu Ser
110                 115                 120
```

(2) INFORMATION FOR SEQ ID NO:8:

(i) SEQUENCE CHARACTERISTICS:
(A) LENGTH: 143 amino acids
(B) TYPE: amino acid
(D) TOPOLOGY: linear (ii) MOLECULE TYPE: protein (xi) SEQUENCE DESCRIPTION: SEQ ID NO:8:

```
Met Asp Trp Thr Trp Arg Val Phe Cys Leu Leu Ala Val Ala Pro Gly
-19             -15                 -10                 -5
```

-continued

```
Ala His Ser Gln Val Gln Leu Gln Glu Ser Gly Pro Gly Leu Val Arg
                1               5                  10

Pro Ser Gln Thr Leu Ser Leu Thr Cys Thr Ala Ser Gly Phe Asn Ile
     15                  20                  25

Lys Asp Thr Tyr Met His Trp Val Arg Gln Pro Pro Gly Arg Gly Leu
 30                  35                  40                  45

Glu Trp Ile Gly Arg Ile Asp Pro Ala Ser Gly Asp Thr Lys Tyr Asp
                    50                  55                  60

Pro Lys Phe Gln Val Arg Val Thr Met Leu Val Asp Thr Ser Ser Asn
                65                  70                  75

Gln Phe Ser Leu Arg Leu Ser Ser Val Thr Ala Ala Asp Thr Ala Val
            80                  85                  90

Tyr Tyr Cys Ala Asp Gly Met Trp Val Ser Thr Gly Tyr Ala Leu Asp
     95                 100                 105

Phe Trp Gly Gln Gly Thr Thr Val Thr Val Ser Ser Gly Glu Ser
110                 115                 120
```

( 2 ) INFORMATION FOR SEQ ID NO:9:

( i ) SEQUENCE CHARACTERISTICS:
( A ) LENGTH: 386 base pairs
( B ) TYPE: nucleic acid
( C ) STRANDEDNESS: single
( D ) TOPOLOGY: linear ( i x ) FEATURE:
( A ) NAME/KEY: sig_peptide
( B ) LOCATION: 1..57

( i x ) FEATURE:
( A ) NAME/KEY: mat_peptide
( B ) LOCATION: 58..384

( i x ) FEATURE:
( A ) NAME/KEY: CDS
( B ) LOCATION: 1..384

( i x ) FEATURE:
( A ) NAME/KEY: misc_feature
( B ) LOCATION: 1
( D ) OTHER INFORMATION: /note= “pBAG198 insert VK2 (SVMDY) light chain variable region”

( x i ) SEQUENCE DESCRIPTION: SEQ ID NO:9:

```
ATG GGT TGG TCC TGC ATC ATC CTG TTC CTG GTT GCT ACC GCT ACC GGT        48
Met Gly Trp Ser Cys Ile Ile Leu Phe Leu Val Ala Thr Ala Thr Gly
-19             -15                 -10                  -5

GTC CAC TCC AGC ATC GTG ATG ACC CAG AGC CCA AGC AGC CTG AGC GCC        96
Val His Ser Ser Ile Val Met Thr Gln Ser Pro Ser Ser Leu Ser Ala
                1               5                  10

AGC GTG GGT GAC AGA GTG ACC ATC ACC TGT AAG GCC AGT CAG AGT GTG       144
Ser Val Gly Asp Arg Val Thr Ile Thr Cys Lys Ala Ser Gln Ser Val
     15                  20                  25

ACT AAT GAT GTA GCT TGG TAC CAG CAG AAG CCA GGT AAG GCT CCA AAG       192
Thr Asn Asp Val Ala Trp Tyr Gln Gln Lys Pro Gly Lys Ala Pro Lys
 30                  35                  40                  45

CTG CTG ATC TAC TAT GCA TCC AAT CGC TAC ACT GGT GTG CCA GAT AGA       240
Leu Leu Ile Tyr Tyr Ala Ser Asn Arg Tyr Thr Gly Val Pro Asp Arg
                    50                  55                  60

TTC AGC GGT AGC GGT TAT GGT ACC GAC TTC ACC TTC ACC ATC AGC AGC       288
Phe Ser Gly Ser Gly Tyr Gly Thr Asp Phe Thr Phe Thr Ile Ser Ser
                65                  70                  75

CTC CAG CCA GAG GAC ATC GCC ACC TAC TAC TGC CAG CAG GAT TAT AGC       336
Leu Gln Pro Glu Asp Ile Ala Thr Tyr Tyr Cys Gln Gln Asp Tyr Ser
            80                  85                  90
```

-continued

| | | | | | | | | | | | | | | | | |
|---|---|---|---|---|---|---|---|---|---|---|---|---|---|---|---|---|
| TCT | CCG | TAC | ACG | TTC | GGC | CAA | GGG | ACC | AAG | GTG | GAA | ATC | AAA | CGT | AAG | 384 |
| Ser | Pro | Tyr | Thr | Phe | Gly | Gln | Gly | Thr | Lys | Val | Glu | Ile | Lys | Arg | Lys | |
| | 95 | | | | | 100 | | | | | 105 | | | | | |
| TG | | | | | | | | | | | | | | | | 386 |

( 2 ) INFORMATION FOR SEQ ID NO:10:

( i ) SEQUENCE CHARACTERISTICS:
( A ) LENGTH: 128 amino acids
( B ) TYPE: amino acid
( D ) TOPOLOGY: linear ( i i ) MOLECULE TYPE: protein ( x i ) SEQUENCE DESCRIPTION: SEQ ID NO:10:

| | | | | | | | | | | | | | | | |
|---|---|---|---|---|---|---|---|---|---|---|---|---|---|---|---|
| Met | Gly | Trp | Ser | Cys | Ile | Ile | Leu | Phe | Leu | Val | Ala | Thr | Ala | Thr | Gly |
| -19 | | | | -15 | | | | | -10 | | | | | -5 | |
| Val | His | Ser | Ser | Ile | Val | Met | Thr | Gln | Ser | Pro | Ser | Ser | Leu | Ser | Ala |
| | | | 1 | | | | 5 | | | | | 10 | | | |
| Ser | Val | Gly | Asp | Arg | Val | Thr | Ile | Thr | Cys | Lys | Ala | Ser | Gln | Ser | Val |
| | 15 | | | | | 20 | | | | | 25 | | | | |
| Thr | Asn | Asp | Val | Ala | Trp | Tyr | Gln | Gln | Lys | Pro | Gly | Lys | Ala | Pro | Lys |
| 30 | | | | | 35 | | | | | 40 | | | | | 45 |
| Leu | Leu | Ile | Tyr | Tyr | Ala | Ser | Asn | Arg | Tyr | Thr | Gly | Val | Pro | Asp | Arg |
| | | | | 50 | | | | | 55 | | | | | 60 | |
| Phe | Ser | Gly | Ser | Gly | Tyr | Gly | Thr | Asp | Phe | Thr | Phe | Thr | Ile | Ser | Ser |
| | | | 65 | | | | | 70 | | | | | 75 | | |
| Leu | Gln | Pro | Glu | Asp | Ile | Ala | Thr | Tyr | Tyr | Cys | Gln | Gln | Asp | Tyr | Ser |
| | | 80 | | | | | 85 | | | | | 90 | | | |
| Ser | Pro | Tyr | Thr | Phe | Gly | Gln | Gly | Thr | Lys | Val | Glu | Ile | Lys | Arg | Lys |
| | 95 | | | | | 100 | | | | | 105 | | | | |